(12) United States Patent
Liao et al.

(10) Patent No.: US 6,696,484 B2
(45) Date of Patent: Feb. 24, 2004

(54) METHOD AND COMPOSITIONS FOR REGULATION OF 5-ALPHA REDUCTASE ACTIVITY

(75) Inventors: Shutsung Liao, Chicago, IL (US); Richard Hiipakka, Chicago, IL (US)

(73) Assignee: University of Chicago Office of Technology and Intellectual Property, Chicago, IL (US)

( * ) Notice: Subject to any disclaimer, the term of this patent is extended or adjusted under 35 U.S.C. 154(b) by 30 days.

(21) Appl. No.: 10/132,050

(22) Filed: Apr. 24, 2002

(65) Prior Publication Data

US 2003/0105030 A1 Jun. 5, 2003

Related U.S. Application Data

(63) Continuation-in-part of application No. 09/530,443, filed as application No. PCT/US98/23041 on Oct. 30, 1998, now Pat. No. 6,576,660.
(60) Provisional application No. 60/063,770, filed on Oct. 31, 1997.

(51) Int. Cl.$^7$ ............................................. A61K 31/35
(52) U.S. Cl. .................... 514/456; 514/337; 514/453; 514/455; 514/457; 514/532; 514/544; 514/557; 514/558; 514/617; 514/622; 514/646; 514/655; 514/678; 514/680; 514/681; 514/682; 514/683; 514/679; 514/720; 514/729; 514/731; 514/732
(58) Field of Search .................... 514/337, 453, 514/455, 456, 457, 532, 544, 557, 617, 622, 655, 646, 690, 680, 678, 683, 558, 681, 682, 679, 720, 729, 731, 732

(56) References Cited

U.S. PATENT DOCUMENTS

| | | |
|---|---|---|
| 5,306,486 A | 4/1994 | McCook et al. |
| 5,422,371 A | 6/1995 | Liao et al. |
| 5,605,929 A | 2/1997 | Liao et al. |
| 5,665,367 A | 9/1997 | Burger et al. |
| 5,665,393 A | 9/1997 | Chen et al. |
| 5,686,082 A | 11/1997 | N'Guyen |
| 5,788,971 A | 8/1998 | Togasaki |
| 5,804,168 A | 9/1998 | Murad |
| 5,804,594 A | 9/1998 | Murad |
| 5,962,517 A | 10/1999 | Murand |
| 6,093,411 A | 7/2000 | Bissett |
| 6,180,662 B1 | 1/2001 | Lansendorfer et al. |
| 6,183,731 B1 | 2/2001 | Carey et al. |
| 6,197,808 B1 | 3/2001 | Cheng et al. |
| 6,231,877 B1 | 5/2001 | Vacher et al. |
| 6,248,341 B1 | 6/2001 | Anderson et al. |
| 6,337,320 B1 | 1/2002 | Hersh et al. |
| 6,391,308 B1 | 5/2002 | Empie et al. |
| 6,395,279 B1 | 5/2002 | Empie et al. |
| 6,471,973 B1 | 10/2002 | Perrier et al. |
| 2002/0122777 A1 | 9/2002 | Zuckerman |
| 2002/0147353 A1 | 10/2002 | Van Der Vijgh, et al. |
| 2002/0176898 A1 | 11/2002 | Moore, et al. |

FOREIGN PATENT DOCUMENTS

| | | |
|---|---|---|
| CN | 1079361 | 12/1993 |
| DE | 19627344 | 1/1998 |
| DE | 29813269 | 11/1998 |
| EP | 0003794 | 9/1979 |
| EP | 0116439 | 8/1984 |
| EP | 0309086 | 3/1989 |
| EP | 0522502 | 1/1993 |
| FR | 2734478 | 11/1996 |
| JP | 57118580 | 7/1982 |
| JP | 57448580 | 7/1982 |
| JP | 62084021 | 4/1987 |
| JP | 1025726 | 1/1989 |

(List continued on next page.)

OTHER PUBLICATIONS

Asai, et al., "Dietary curcuminoids prevent high–fat diet–induced lipid accumulation in rat liver and epididymal adipose tissue," J. Nutr, 2001, 131(11):2932–5.
Bhattacharyya et al., "Analysis of the steroid binding domain of rat steroid 5 alpha–reductase (isozyme–1) the steroid D–ring binding domain of 5 alpha–reductase," Steroids, 1999; 64: 197–204.
Deplewski, et al., "Preputial sebocyte 5 alpha–reductse isoform specificity," Endocrinology, 1997, 138 (10): 4416–20.
Donadio, James V., "Omega–3 polyunsaturated fatty acids: a potential new treatment of immune reanl disease," Mayo Clin Proc, May 1991: 1018–1028.
Downing, et al., "Essential fatty acids and acne," J Am Acad Dermatrol, 6; May 1986: 221–5.
Frost, et al., "Inhibitors of sex hormones: development of experiment modes", Adv. Biol. Skin., May 1972: 403–420.
Harris, et al., "Identification oand selective inhibition of an isozyme of steroid 5 alpha–reductase in human scalp," Prc. Natl. Acad. Sci. USA, May 1992: 10787–1079.
Hiipakka, et al., "Structure–activity relationship for inhibition of human 5 alpha–reductase by polyphenols," Biochem Pharmacol. Mar. 15, 2002;63(6): 1165–76.
Hiipakka, et al., "Expression of 5 alpha–reductase in bacteria as a trp E fusion protein and its use in the production of antibodies for immunocytochemical localization of 5 alpha reductase," J Steroid Biochem Mol Biol. Jun. 1993;45(6): 539–48.

(List continued on next page.)

*Primary Examiner*—Amelia Owens
(74) *Attorney, Agent, or Firm*—Joseph A. Mahoney; Christine M. Rebman; Mayer Brown Rowe & Maw LLP

(57) ABSTRACT

Pharmaceutical compositions and methods for treating androgen related disorders. The pharmaceutical compositions may include a 5α-reductase inhibitor, such as natural and synthetic flavanoids, catechols, curcumin-related substances, quinones, catechins, particularly epigallocatechin derivatives, fatty acids, and the salts, esters, analogues, pro-drugs, isomers, racemic mixtures, or derivatives of any of the foregoing. The use of testosterone (or DHT) combinations with the aforementioned 5α-reductase inhibitor compounds is also contemplated.

57 Claims, 20 Drawing Sheets

FOREIGN PATENT DOCUMENTS

| | | |
|---|---|---|
| JP | 2300120 | 12/1990 |
| JP | 5139987 | 6/1993 |
| JP | 5279264 | 10/1993 |
| JP | 6128168 | 5/1994 |
| JP | 6172122 | 6/1994 |
| JP | 9315985 | 12/1997 |
| WO | WO 94/01100 | 1/1994 |
| WO | WO 94/09801 | 5/1994 |
| WO | WO 96/37201 | 11/1996 |
| WO | 9637201 | 11/1996 |
| WO | WO 99/22728 | 5/1999 |
| WO | 9922728 | 5/1999 |
| WO | WO 00/61547 | 10/2000 |
| WO | 0126668 | 4/2001 |
| WO | WO 01/26668 | 4/2001 |
| WO | 0149285 | 7/2001 |
| WO | WO 01/49285 | 7/2001 |
| WO | 0160319 | 8/2001 |
| WO | WO 01/72318 | 10/2001 |
| WO | 0172318 | 10/2001 |
| WO | 0172319 | 10/2001 |
| WO | WO 01/72319 | 10/2001 |
| WO | 0174327 | 10/2001 |
| WO | WO 01/74327 | 10/2001 |
| WO | 0265846 | 8/2002 |

OTHER PUBLICATIONS

Igarashi, Miki and Miyazawa, Teruo, "The growth inhiitory effect of conjugated linoliec acid on a human hepatoma cell line, HepG2, is induced by achange in fatty acid metabolism, but not the facilitation of lipid peroxidation in the cells," Biochem Biophys Acta. Feb. 26, 2001;1530(2–3): 162–71.

Kao, et al., "Modulation of obesity by a green tea catechin," Am J Clin Nutr. Nov. 2000;72(5): 1232–4.

Horrobin, et al., "Essential fatty acids in clinical dermatology," J Am Acad Dermatol. Jun. 1989; 20(6):1045–53.

Khan, et al., "Arachidonic and cis–unsaturated fatty acids induce selective platelet substrate phosphorylation through activation of cytosolic protein kinase C," FEBS Lett. Nov. 4, 1991;292(1–2):98–102.

Komori, et al., "Anticarcinogenic activity of green tea polyphenols," Jpn J Clin Oncol. Jun. 1993;23(3):186–90.

Liang, et al., "Inhibition of testosterone stimulation of the hamster flank organs by y–linolenic acid a five alpha–reductase inhibitor," SID Abstracts, vol. 102 (No. 4), 647.

Liang, et al., "Species differences in prostatic steroid 5 alpha–reductases of rat, dog, and human," Endocrinology. Aug. 1985;117(2):571–9.

Liang, Techming and Liao, Shutsung, "Inhibition of steroid 5 alpha–reductase by specific aliphatic unsaturated fatty acids," Biochem J. Jul. 15, 1992;285 (Pt 2):557–62.

Liang, et al., "Anti–5 alph–reductase autoantibodies in the serum of patients with prostatic cancer," J Clin Endocrinol Metab. Dec. 1990;71(6):1666–8.

Liang, et al., "Growth suppression of hamster flank organs by topical application of y–linolenic and other fatty acid inhibitors of 5 alpha–reductase," J Invest Dermatol. Aug. 1997;109(2):152–7.

Liao, et al., "Growth inhibition and regression of human prostate and breast tumors in athymic mice by tea epigallocatechin gallate," Cancer Lett. Sep. 25, 1995;96(2):239–43.

Liao, S, "The medicinal action of androgens and green tea epigallocatechin gallate," Hong Kong Med J. Dec. 2001;7(4): 369–74.

Liao, et al., "Growth suppression of hamster flank organs by topical application of catechins, alizarin, curcumin, and myristoleic acid," Arch Dermatol Res. Apr. 2001;293(4): 200–5.

Shutsung, Liao, "Androgen action: Molecular mechanism and medical application," J Formos Med Assoc. Sep. 1994;93(9): 741–51.

Liao, et al., "Selective inhibition of steroid 5 alpha–reductase isozymes by tea ipicatechin–3–gallate and epicallocatechin–3–gallate," Biochem Biophys Res Commun. Sep. 25, 1995;214(3):833–8.

Liao, et al., "Green tea: Biochemical and biological bais for health benefits," Vitam Horm. 2001;62:1–94.

Miyazawa, Teruo, "Absorption, metabolism and antioxidative effects of tea catechin in humans," Biofactors. 2000;13(1–4):55–9.

Nagata, et al., "Association of coffee, green tea, and caffine intakes with serum concentrations of estriadiol and sex hormone–binding globulin in premenopausal japanese women,"Nutr Cancer. 1998;30(1):21–4.

Rose, David and Connolly, Jeanne, "Effects of fatty acids and dicosanoid synthesi inhibitors on the growth of two human prostate cancer cell lines," Prostate. 1991;18(3):243–54.

Rizvi, Syed and Zaid, Mohammad, "Modulation of erythrocyte membrane NA/K–Atpase activity by insulin in normal and type 2 diabetic patients. evaluation of the insulin–like role of (–)epicatechin," Medicinal Science Research. 1998. 26:245–247.

Serafini, Paulo and Lobo, Rogerio, "Increased 5alpha–reductase activity in idiopathic hirsutism," Fertil Steril. Jan. 1985;43(1): 74–8.

Tang, et al., "Green tea polyphenols and vitamin e inhibit angogenesis by supressing il–8," Free Radic Biol Med. 1999. 27: S149.

Taylor, et al., "Photoaffinity labeling or rat steroid 5alpha–reductase (isozyme–1) by a benzophenone derivative of a 4–methyl–4–azasteroid," Steroids. May 1996;61 (5):323–31.

Umekita, et al., "Human prostate tumor growth in athymic mice: inhibition by androgens and stimulation by finasteride," Proc Natl Acad Sci U S A. Oct. 15, 1996;93(21):11802–7.

Valcic, et al., "Inhibitory effect of six green tea catechins and caffeine on the growth of four selected human tumor cell lines," Anticancer Drugs. Jun. 1996;7(4):461–8.

Yang, Chung and Wang, Zhi–Yuan, "Tea and cancer," J Natl Cancer Inst. Jul. 7, 1993;85(13):1038–49.

Zhu, et al., "Effects of tea polyphenols and flavonoids on liver microsomal glucuronidation of estradiol and estrone," J Steroid Biochem Mol Biol. Feb. 1998;64(3–4):207–15.

Chantre P. and Lairon D., "Recent findings of green tea extract AR25 (exolise and its activity for the treatment of obesity," Phytomedicine (jena), Jan. 2002; 9(1); 3–8.

Sartippour, et al., "Green tea and its catechins inhibit breast cancer xenografts," Nutrition and Cancer. 2001; 40 (2);149–156.

Proniuk, et al., "Preformulation study of epigallocatechin gallate, a promising antioxidant for topical skin cancer prevention." J. Pharm Sci. Jan. 2002; 91; 111–6.

Kao, et al., "Modulation of endocrine systems and food intake by green tea epigallocatechin gallate". Endocrinology, 2000, 141 (3): 980–987.

Fujiki, et al., *Green Tea: Cancer Preventive Beverage and/or Drug, Cancer Letters*, vol. 188, pp. 9–13 (2002).

Le Marchand, *Cancer Preventive Effects of Flavonoids—A Review, Biomed Pharmacother*, vol. 56, pp. 296–301 (2002).

Lou, et al., *Effects of Topical Applications of Caffeine or (–)—Epigallocatechin Gallate (EGCG) on Skin Carcimogenesis and Apoptosis in SKH–1 Hairless Mice Previously Treated with Ultraviolet B Light (High Risk Mice)*, Proceedings of the American Association for Cancer Research, vol. 43, p. 1143 (Mar. 2002).

Ahmed, et al., *Differential Modulation of Growth and Glutathione Metabolism in Cultured Rat Astrocytes by 4–Hydroxynonenal and Green Tea Polyphenol, Epigallocatechin–3–Gallate*, Neuro Toxicology, vol. 23, pp. 289–300 (2002).

Cai, et al., *Contribution of Presystemic Hepatic Extraction to the Low Oral Bioavailability of Green Tea Catechins in Rats*, Drug Metabolism and Disposition, vol. 30, pp. 1246–1249 (2002).

Soleas, et al., *A Comparison of the Anticarcinogenic Properties of Four Red Wine Polyphenols*, Clinical Biochemistry, vol. 35, pp. 119–124 (2002).

Proniuk, et al., *Preformulation Study of Epigallocatechin Gallate, a Promising Antioxidant for Topical Skin Cancer Prevention*, Journal of Pharmaceutical Sciences, vol. 91, No. 1, pp. 111–116 (Jan. 2002).

Getie, et al., *Evaluation of the Release Profiles of Flavonoids from Topical Formulations of the Crude Extract of the Leaves of Dodonea Viscosa (Sapindaceae)*, Pharmazie, vol. 57, pp. 320–322 (2002).

Wang, et al., *Gene Expression Profile in Human Prostate LNCaP Cancer Cells by (–) Epigallocatechin–3–Gallate*, Cancer Letters, vol. 182, pp. 43–51 (2002).

Greenway, *Non–Pharmacologic Treatment of Obesity: Herbal Aids to Weight Loss*, International Journal of Obesity, S185, No. 693.

*Tea Offers Myriad Health Benefits*, www.msnbc (downloaded Sep. 27, 2002).

Gupta, et al., *Inhibition of Prostate Carcinogenesis in TRAMP Mice by Oral Infusion of Green Tea Polyphenols*, PNAS, vol. 96, No. 18 (Aug. 28, 2001).

Kao, et al., *Modulation of Endocrine Systems and Food Intake by Green Tea Epigallocate Gallate*, Endocrinology, vol. 141, No. 3, pp. 980–987 (2000).

Dulloo, *Reply to Y–H Kao, et al.*, The American Journal of Clinical Nutrition, vol. 72, No. 5, pp. 1233–34 (Nov. 2000).

Dulloo, et al., *Efficacy of a Green Tea Extract Rich in Catechin Polyphenols and Caffeine in Increasing 24–h Energy Expenditure and Fat Oxidation in Humans*, American Journal of Clinical Nutrition, vol. 70, No. 6, pp. 1040–45 (Dec. 1999).

Chantre, et al., *Recent Findings of Green Tea Extract AR25 (Exolise) and its Activity for the Treatment of Obesity*, Phytomedicine, vol. 9, pp. 3–8 (2002).

Dulloo, et al., *Green Tea and Thermogenesis: Interactions Between Catechin–Polyphenols, Caffeine and Sympathetic Activity*, International Journal of Obesity Related Metabolic Disorders, vol. 24, No. 2, pp. 252–8 (Feb. 2000) [Abstract].

Miyazawa, *Absorption, Metabolism and Antioxidative Effects of Tea Catechin in Humans*, BioFactors, vol. 13, pp. 55–59 (2000).

Nagata, et al., *Association of Coffee, Green Tea, and Caffeine Intakes With Serum Concentrations of Estradiol and Sex Hormone–Binding Globulin in Premenopausal Japanese Women*, Nutrition and Cancer, vol. 30, No. 1, pp. 21–24 (1998).

Tang, et al., *Green Tea Polyphenols and Vitamin E Inhibit Angiogenesis by Suppressing IL–8*, Oxygen, S149, No. 456 (1999).

Komori, et al., *Anticarcinogenic Activity of Green Tea Polyphenols*, Japanese Journal of Clinical Oncology, vol. 23, No. 3, pp. 186–190 (1993).

*Green Tea Inhibits Factor Linked to Vessel Growth in Cancer*, www.Bioexchange.com (Downloaded Nov. 1, 2002).

Asai, et al., *Dietary Curcuminoids Prevent High–Fat Diet–Induced Lipid Accumulation in Rat Liver and Epididymal Adipose Tissue*, J. Nutr., vol. 131, No. 11, pp. 2932–5 (Nov. 2001). [Abstract].

Nakagawa, et al., *Dose–Dependent Incorporation of Tea Catechins, (–)–Epigallocatechin–3–Gallate and (–)–Epigallocatechin, Into Human Plasma*, Biosci Biotechnol Biochem, vol. 61, No. 12, pp. 1981–5 (Dec. 1997). [Abstract].

Sartippour, et al., *Green Tea and Its Catechins Inhibit Breast Cancer Xenografts*, Nutrition and Cancer, vol. 40, No. 2, pp. 149–156 (2001).

Zhu, et al., *Effects of Tea Polyphenols and Flavonoids on Liver Microsomal Glucuronidation of Estradiol and Estrone*, J. Steroid Biochem. Molec. Biol., vol. 64, No. 3–4, pp. 207–215 (1998).

Yang, et al., *Tea and Cancer*, Journal of National Cancer Institute, vol. 85, No. 13, pp. 1038–1049 (Jul. 7, 1993).

Valcic, et al., *Inhibitory Effect of Six Green Tea Catechins and Caffeine on the Growth of Four Selected Human Tumor Cell Lines*, Anti–Cancer Drugs, vol. 7, pp. 461–468 (1996).

Umekita, et al., *Human Prostate Tumor Growth in Athymic Mice: Inhibition by Androgens and Stimulation by Finasteride*, Proc. Natl. Acad. Sci. USA, vol. 93, pp. 11802–11807 (Oct. 1996).

Liao, et al., *Green Tea: Biochemical and Biological Basis for Health Benefits*, Vitamins and Hormones, vol. 62, pp. 1–94 (2001).

Liao, et al., *Selective Inhibition of Steroid 5α–Reductase Isozymes by Tea Epicatechin–3–Gallate and Epigallocatechin–3–Gallate*, Biochemical and Biophysical Research Communications, vol. 214, No. 3, pp. 833–838 (1995).

Liao, et al., *Growth Suppression of Hamster Flank Organs by Topical Application of Catechins, Alizarin, Curcumin, and Myristoleic Acid*, Arch Dermatol Res., vol. 293, pp. 200–205 (2001).

Liao, *The Medicinal Action of Androgens and Green Tea Epigallocatechin Gallate*, HKMJ, vol. 7, No. 4, pp. 369–374 (Dec. 2001).

Liao, et al., *Growth Inhibition and Regression of Human Prostate and Breast Tumors in Athymic Mice by Tea Epigallocatechin Gallate*, Cancer Letters, vol. 96, pp. 239–243 (1995).

Willett, *Modulation of Obesity by a Green Tea Catechin*, Am. J. Clin. Nutr., vol. 72, pp. 1232–1235 (2000).

Hiipakka, et al., *Structure–Activity Relationships for Inhibition of Human 5α–Reductase by Polyphenols*, Biochemical Pharmacology, vol. 63, pp. 1165–76 (2002).

Afaq, et al., *Green Tea Polyphenol (–)–Epigallocatechin–3–Gallate Inhibits Ultra–Violet B–Mediated Activation of Nuclear Factor kB in Cultured Human Epidermal Keratinocytes*, Proceedings of the American Association for Cancer Research, vol. 43, p. 1143, No. 5665 (Mar. 2002).

FIGURE 1 - FLAVANOIDS
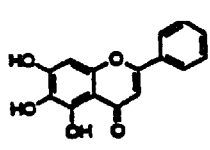
BAICALEIN
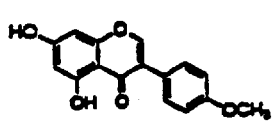
BIOCHANIN A
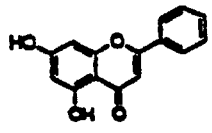
CHRYSIN
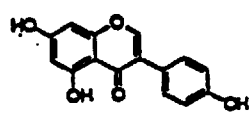
DAIDZEIN
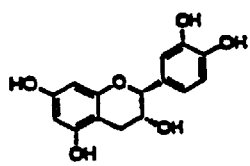
EPICATECHIN
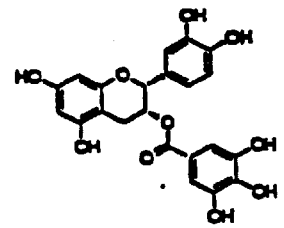
EPICATECHIN GALLATE
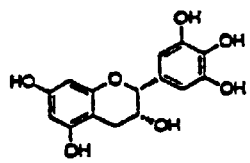
EPIGALLOCATECHIN
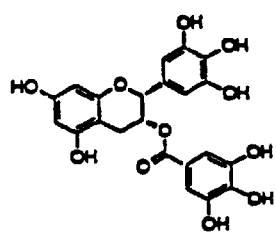
EPIGALLOCATECHIN GALLATE
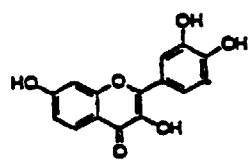
FISETIN
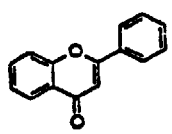
FLAVONE
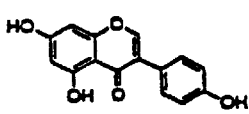
GENISTEIN
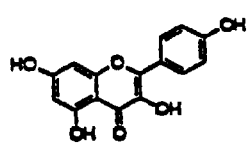
KAEMPFEROL
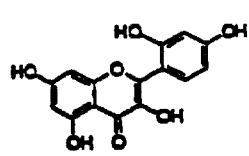
MORIN
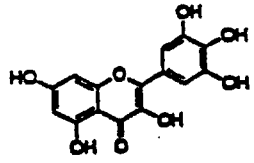
MYRICETIN
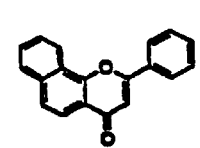
α-NAPTHOFLAVONE
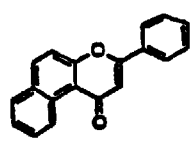
β-NAPTHOFLAVONE
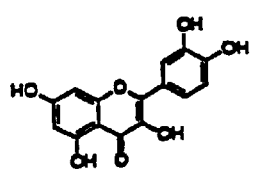
QUERCITIN
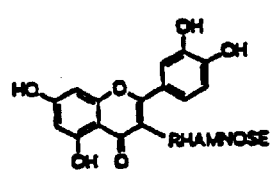
RUTIN
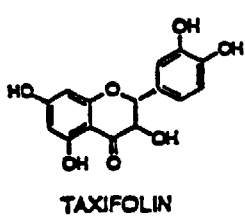
TAXIFOLIN FIGURE 2 - CATECHOLS
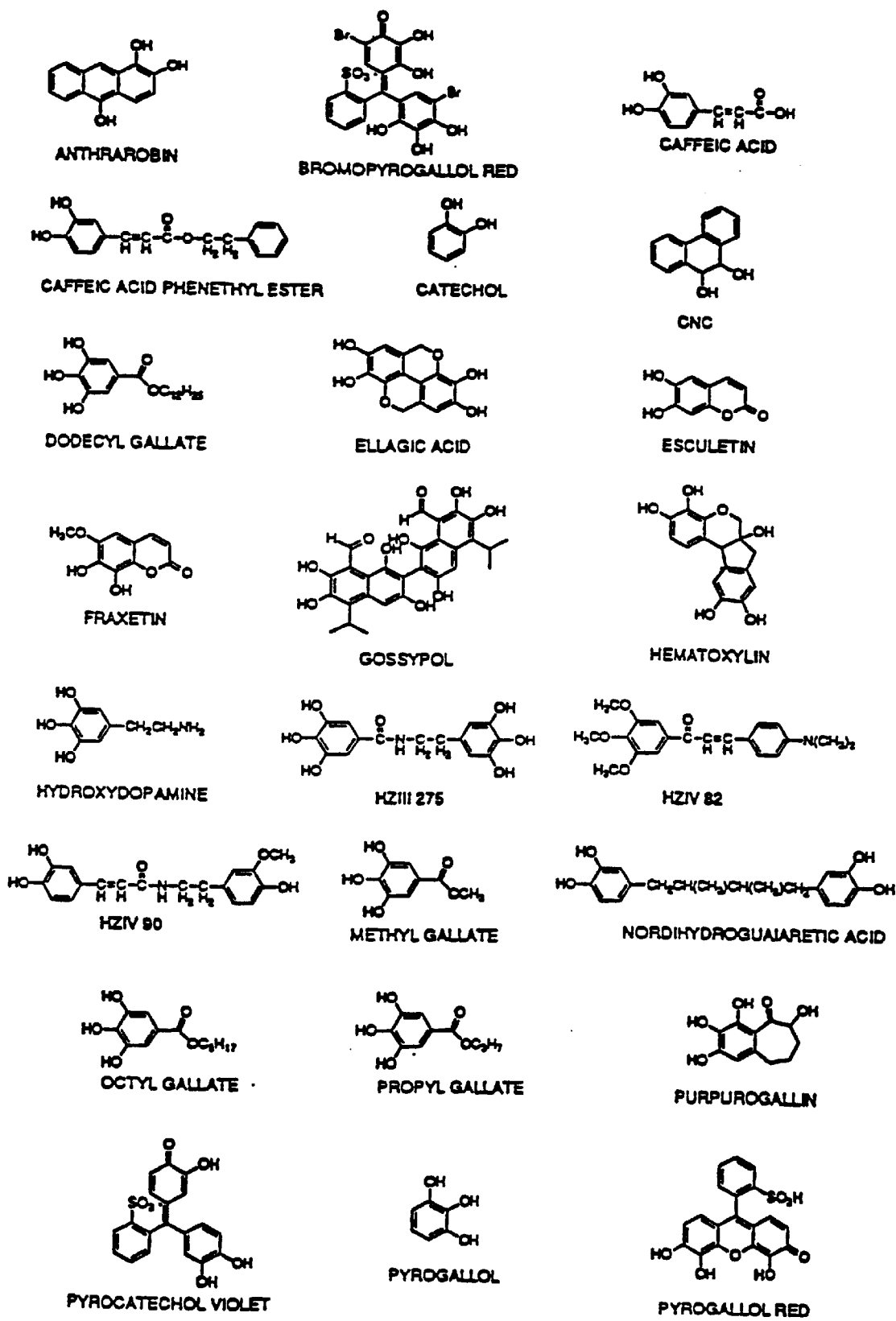

FIGURE 3 - FERULIC ACID DERIVATIVES
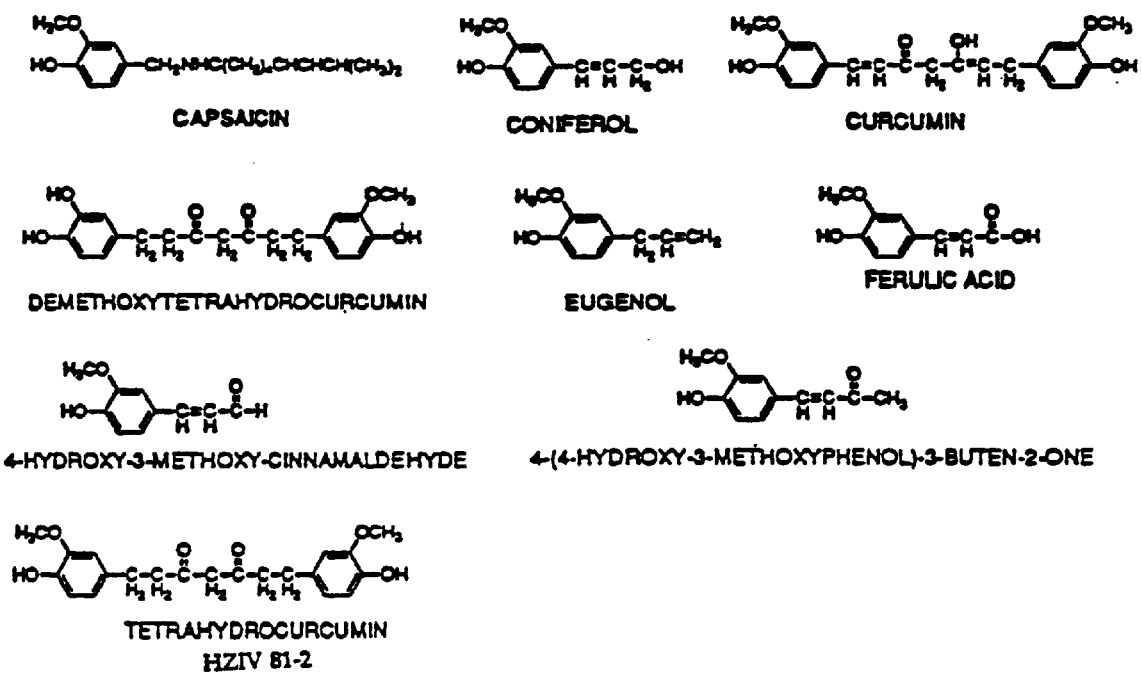

FIGURE 4 - QUINONES
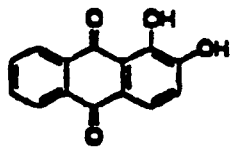
ALIZARIN
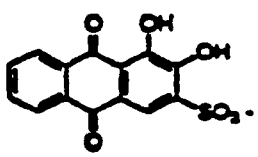
ALIZARIN RED S
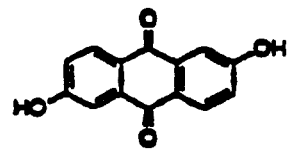
ANTHRAFLAVIC ACID
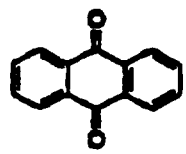
ANTHRAQUINONE
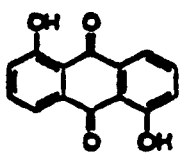
ANTHRARUFIN
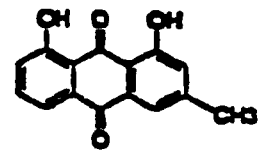
CHRYSOPHANIC ACID
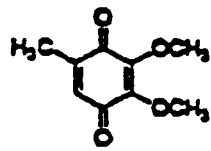
COENZYME $Q_1$
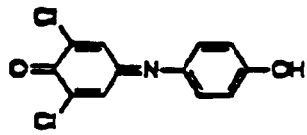
2,6-DICHLOROINDOPHENOL
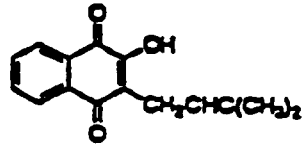
LAPACHOL
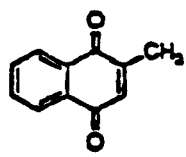
MENADIONE
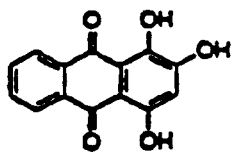
PURPURIN
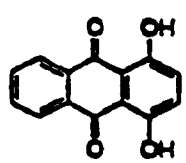
QUINIZARIN
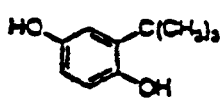
t-BUTYLHYDROQUINONE

FIGURE 5 - EPIGALLOCATECHIN DERIVATIVES

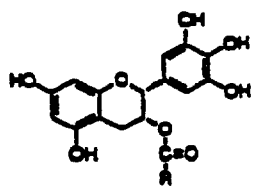

| COMPOUND | R |
|---|---|
| EGCG | 3,4,5-trihydroxyphenyl |
| EGC | H |
| HZIV 109 | OH |
| HZIV 145 | CH₃ |
| HZIV 169 | CH₃(CH₂)₄ |
| HZIV 166 | CH₃(CH₂)₆ |
| HZIV 168 | (C₉H₁₇) alkenyl |
| HZIV 165 | CH₃(CH₂)₁₂ |
| HZIV 160 | (C₁₃H₂₅) alkenyl |
| HZIV 148 | CH₃(CH₂)₁₆ |
| HZIV 142 | (C₁₇H₂₉) polyunsaturated |
| HZIV 144 | (CYCLOHEXYL) |
| HZIV 74 | phenyl |
| HZIV 107 | 4-pyridyl |
| HZIV 92 | 4-(H₃C)₂N-phenyl |
| HZIV 120 | 2-naphthyl |
| HZIV 63 | 3,4,5-trimethoxyphenyl |
| HZIV 68 | 3,5-dihydroxy-4-methyl-phenyl (H₃C, HO substituted) |
| HZIV 75 | 3,5-dimethoxy-4-hydroxyphenyl |
| HZIV 134 | 3,4,5-trihydroxyphenyl-CH=CH- |

FIGURE 6 -
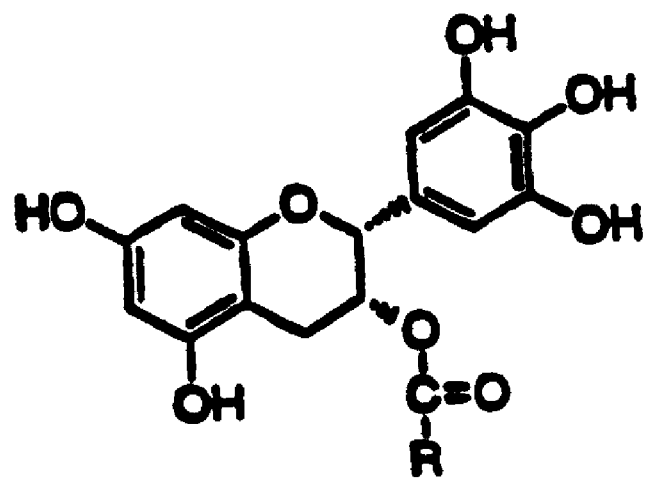

FIGURE 9
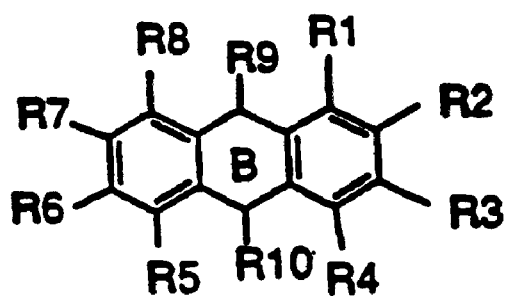
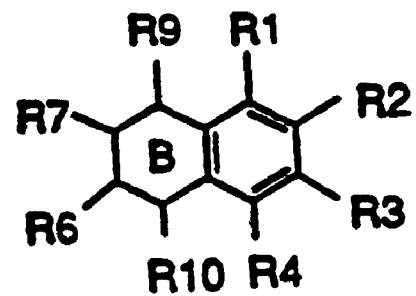

FIGURE 10 - FATTY ACIDS
CONJUGATED OCTADECADIENIOC ACID:
MIXTURE OF CIS AND TRANS 9,11 AND 10,12
OCTADECADIENOIC ACIDS (C18:2)
5,8,11,14-EICOSATETRAYNOIC ACID
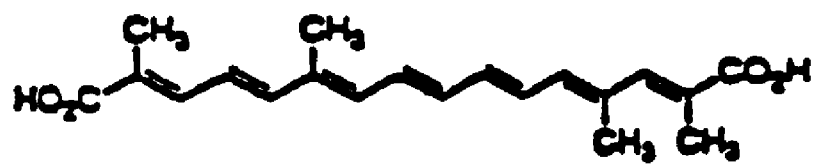
CROCETIN Fig. 11
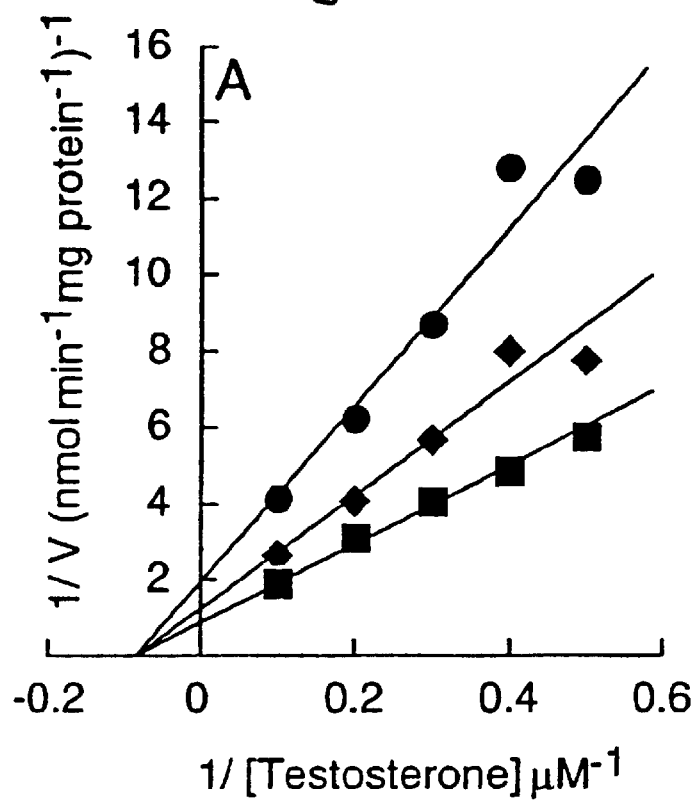
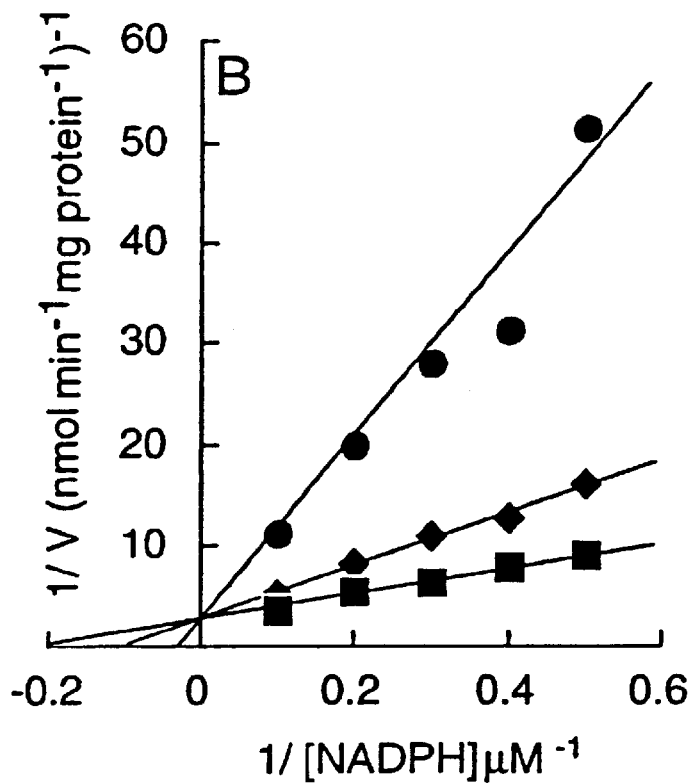

METHOD AND COMPOSITIONS FOR REGULATION OF 5-ALPHA REDUCTASE ACTIVITY

CROSS-REFERENCES TO RELATED APPLICATIONS

This application is a continuation-in-part of U.S. patent application Ser. No. 09/530,443, filed on Apr. 28, 2000, now U.S. Pat. No. 6,576,660 B1 which is a 371 and claims priority to International Application No. PCT/US98/23041, filed on Oct. 30, 1998, which claims priority to U.S. Provisional Application Ser. No. 60/063,770, filed on Oct. 31, 1997. This application claims priority to all such previous applications, and such applications are hereby incorporated herein by reference.

TECHNICAL FIELD OF THE INVENTION

The present invention relates generally to compounds, compositions and methods regulating the action and function of androgens and other steroid hormones by modulating the activity of steroid-reductases, including isozymes of α-reductases.

BACKGROUND OF THE INVENTION

In some of the androgen-sensitive organs, such as the prostate and skin, testosterone (T) is converted to a more active metabolite 5α-dihydrotestosterone (DHT) by 5α-reductase (Anderson and Liao, 1968; Bruchovsky and Wilson, 1968). Other substrates of 5α-reductases are also converted to reduce products that may have specific properties. Inhibition of 5α-reductase represents a unique approach for developing therapeutic methods for androgen-dependent diseases, such as benign prostatic hyperplasia, breast and prostatic cancer, skin disorders, seborrhea, common baldness, hirsutism, and hidradenitis suppurative. Various compounds have been shown to inhibit 5α-reductase activity (Liang and Liao, 1992; Hirsch et al., 1993; Russell and Wilson, 1994; Liao and Hiipakka, 1995). Finasteride (Proscar), a 5α-reductase inhibitor, lowers the level of DHT in serum and the prostate, reduces prostate volume and increases urinary flow in some patients (Stoner E. Finasteride Study Group, 1992). Certain aliphatic unsaturated fatty acids, such as γ-linolenic acid (Liang and Liao, 1992) and catechin-3-gallates (Liao and Hiipakka, 1995), can inhibit 5α-reductase activity of liver and prostate of rats and humans in vitro.

5α-Reductase is found in many organs (Russell and Wilson, 1994; Hiipakka et al., 1993) including the sebaceous gland of hamsters (Takayasu and Adachi, 1972) and human hair follicles (Randall, 1994). Two 5α-reductase isozymes have been identified in rats and humans (Russell and Wilson, 1994). The type 1 isozyme predominates in rat tissues such as liver, kidney, brain, and lung, whereas the type 2 enzyme is more abundant in rat testis and epididymis. Both isozymes are found in skins of the neonate, but the type 1 isozyme is the major form expressed in the skin after puberty. The type 1 isozyme is also expressed in balding scalp. The possibility that the type 2 isozyme plays a unique role in skin and hair growth cannot be excluded. Finasteride, a 4-azasteroid, is a competitive inhibitor of 5α-reductases and has an affinity 30-fold higher for isozyme 2 than for isozyme 1 (Russell and Wilson, 1994). In contrast, the green tea catechins, epicatechin-3gallate and epigallocatechin-3-gallate are more effective inhibitors of the type 1 enzyme and γ-linolenic acid inhibits both isozymes equally well (Liao and Hiipakka, 1995).

In the stumptail macaque, a monkey model of androgenic alopecia, finasteride given orally prevents frontal baldness (Diani et al, 1992). The paired hamster flank organs, one on each side of the costovertebral angle, are highly sensitive to androgen stimulation. Topical application of γ-linolenic acid suppresses only the androgen-dependent growth of the treated hamster flank organ without showing systemic effects on the contralateral flank organ and this effect is very likely due to local inhibition of 5α-reductase.

Uses of androgens known to the medical arts include, for example, treatment of hypogonadism and anemia. The abuse of androgens among athletes to enhance performance is well known. Androgens are also known to promote the development of benign prostatic hyperplasia (BPH), prostate cancer, baldness, acne, obesity and undesirable lipid and steroid profiles in blood and organs. Approximately 70% of males in the U.S. over the age of 50 have pathological evidence of BPH. Prostate cancer is the second leading cause of cancer death in males in the U.S. Male-pattern baldness can start as early as the teens in genetically susceptible males, and it has been estimated to be present in 30% of Caucasian males at age 30, 40% of Caucasian males at age 40, and 50% of Caucasian males at age 50. Further, acne is the most common skin disorder treated by physicians. In women, hirsutism is one of the hallmarks of excessive androgen. The ovaries and the adrenal are the major sources of androgen in women.

In men, the major androgen circulating in the blood is testosterone. About 98% of the testosterone in blood is bound to serum proteins (high affinity binding to sex-steroid binding globulin and low affinity binding to albumin), with only 1–2% in free form. The albumin-bound testosterone, the binding of which is readily reversible, and the free form are considered to be bioavailable, and account for about 50% of total testosterone. Testosterone enters target cells apparently by diffusion. In the prostate, seminal vesicles, skin, and some other target organs, it is converted by a NADPH-dependent 5α-reductase to a more active metabolite, 5α-DHT. 5α-DHT then binds an androgen receptor (AR) in target organs. The 5α-DHT-receptor complexes interact with specific portions of the genome to regulate gene activities (Liao et al., 1989). Testosterone appears to bind to the same AR, but it has a lower affinity than 5α-DHT. In tissues such as muscle and testes, where 5α-reductase activity is low, testosterone may be the more active androgen.

The difference between testosterone and 5α-DHT activity in different androgen-responsive tissues is further suggested by findings in patients with 5α-reductase deficiency. Males with 5α-reductase deficiency are born with female-like external genitalia. When they reach puberty, their plasma levels of testosterone are normal or slightly elevated. Their muscle growth accelerates, the penis enlarges, voice deepens, and libido toward females develops. However, their prostates remain non-palpable, they have reduced body hair, and they do not develop acne or baldness.

The findings in 5α-reductase deficient patients suggest that inhibitors of 5α-reductase would be useful for the treatment of prostatic cancer, BPH, acne, baldness, and female hirsutism. Clinical observations and animal experiments have indicated that spermatogenesis, maintenance of libido, sexual behavior, and feedback inhibition of gonadotropin secretion do not require the conversion of testosterone to 5α-DHT. This is in contrast to other hormonal therapies which abolish the actions of both testosterone and 5α-DHT.

Treatment of androgen-dependent skin and prostatic diseases by 5α-reductase inhibitors would be expected to produce fewer side effects than the presently available hormonal therapies. These include castration, estrogen therapy, high doses of superactive gonadotropin-releasing hormone such as Luprolide, and the use of competitive antiandrogens which inhibit AR binding of testosterone and 5α-DHT, such as flutamide, cyproterone acetate and spironolactone. The long term efficacy of competitive antiandrogens is also compromised by their block of the androgenic feedback inhibition of gonadotropin secretion. This increases testicular secretion of testosterone. The higher level of testosterone eventually overcomes the action of the antiandrogen.

Excessive 5α-DHT is implicated in certain androgen-dependent pathological conditions including BPH, acne, male-pattern baldness, and female idiopathic hirsutism. It has been shown that 5α-reductase activity is reported to be higher in hair follicles from the scalp of balding men than that of non-balding men.

Since normal or slightly elevated plasma levels of testosterone in 5α-reductase deficient males produce beneficial effects, it is desirable to provide agents that inhibit particular androgen action while maintaining normal testosterone levels.

BRIEF SUMMARY OF THE INVENTION

The present invention relates to pharmaceutical compositions and methods for treating androgen related disorders. The pharmaceutical compositions may include a 5α-reductase inhibitor, such as natural and synthetic flavanoids, catechols, curcumin-related substances, quinones, catechins, particularly epigallocatechin derivatives, fatty acids, and the salts, esters, analogues, pro-drugs, isomers, racemic mixtures, or derivatives of any of the foregoing. The inventive compositions may alternatively comprise mixtures of more than one 5α-reductase inhibitor. In certain aspects, these compounds are employed to repress androgenic activity by inhibiting the formation and availability of active androgen in target cells. Consequently, the present invention is useful for the treatment of a wide variety of conditions including, but not limited to, the treatment of prostatic hyperplasia, prostatic cancer, breast cancer, skin cancer and other skin diseases, hirsutism, male pattern baldness, seborrhea, obesity, and other diseases related to lipid synthesis, body weight, and/or androgen function. Several of these compounds have been shown to effectively decrease body weight, and in some cases, to decrease the weight of an androgen-dependent body organ, such as the prostate and other organs. The effectiveness of these compounds may be dependent also on their action on other mechanisms involved in angiogenesis, cell—cell interaction, and on their interaction with various components of organs and cells.

Compounds useful in the practice of the present invention include various isomers of saturated and unsaturated fatty acids, their natural and synthetic analogues and derivatives from which these fatty acids can be generated as well as the metabolites and oxidation products of these fatty acids. The use of these and other fatty acids and their derivatives is also contemplated. Also useful are catechin compounds, particularly, catechins that are structurally similar to epicatechin gallate (ECG) and epigallocatechin gallate (EGCG). EGCG has an additional hydroxyl group compared to the epicatechin gallate molecule, which has been found to be surprisingly active in modulating several 5α-reductase mediated processes. EGCG derivatives having such an additional OH group were shown to be active in inducing body weight loss and particularly in reducing the size of androgen sensitive organs such as preputial glands, ventral prostate, dorsolateral prostate, coagulating glands, seminal vesicles, human prostate tumors, and breast tumors in nude mice.

In more particular aspects of the invention, the inventors have discovered that certain catechins, particularly EGCG, can be administered to promote body weight loss that differentially affects overall body weight and prostate weight loss. In particular examples, it was shown that for a certain percentage of overall body weight loss, prostate weight loss was percentage-wise more than three times as much. The loss in body weight and the organ weight are likely due to EGCG interference of a common step in the pathway controlling body weight and the organ weight gain. EGCG and related compounds may interact and interfere with a receptor macromolecule (probably containing a protein) that modulates specific lipid synthesis and accumulation. Lipids can modulate gene expression, cell development and differentiation, and organ growth. Specific interference of lipid metabolism in the cells and organs may control the growth of the organs, in particular, prostate, sebaceous, preputial and other secretory organs. In certain applications, it is expected that benign or abnormal growth or cancer of these organs may be treated or even prevented by administration of catechin related compounds.

It has been demonstrated that catechin compounds will arrest or reduce human prostate and breast cancer cell growth. The effectiveness of catechin compounds was shown to be dependent on the methods by which these compounds were administered to the experimental animals. Intraperitoneal application was much more effective than oral administration. It is expected that direct application to the organs, such as the prostate, will be very effective. EGCG was surprisingly effective in suppressing and even reducing the size of human prostate and breast tumors in animal models. The effect was illustrated with EGCG; however, structurally similar catechin compounds are also effective, particularly those that are structurally similar to EGCG in having at least one additional hydroxyl group as compared with ECG. Thus, the EGCG species that contains eight hydroxyl groups is significantly more effective in reducing body weight than is ECG, which contains seven hydroxyl groups. Compounds of this general structure are expected to be particularly effective in chemoprevention and chemotherapy of human prostate cancer. Compounds having a structure similar to a part of structure of EGCG are also expected to be effective.

Compounds can be used as antiandrogenic agents through topical or systemic application. A preparation for this purpose can include a carrier, a protectant, an antioxidant (such as vitamin C or E, and various catechins and polyphenols), and other pharmaceutical and pharmacological agents. It is also expected that such compounds can be used in a delivery system (oral, local application, injection, or implantation) involving molecular recognition through which the compounds are delivered to target sites. Such a delivery system may involve, among other methods, liposome techniques or immunological devices.

The present invention also relates to novel compounds. These compounds have the formula:

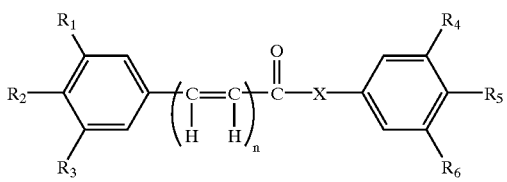

where x is —NHCH$_2$CH$_2$— or —CH=CH—;

R$_1$, R$_2$ and R$_3$ each may be —H, —OH or —OCH$_3$, provided that only one of R$_1$, R$_2$, and R$_3$ may be —H;

R$_4$, R$_5$ and R$_6$ each may be —H, —OH, —OCH$_3$ or —N(CH$_3$)$_2$, provided that only one of R$_4$, R$_5$ and R$_6$ may be —H; and n is 0 or 1.

Further, the epigallocatechin derivatives may have the formula:

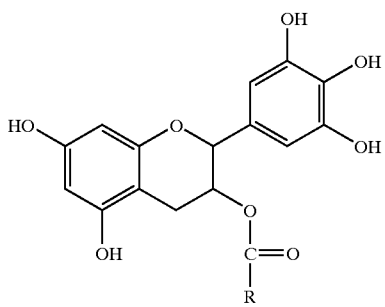

where R is

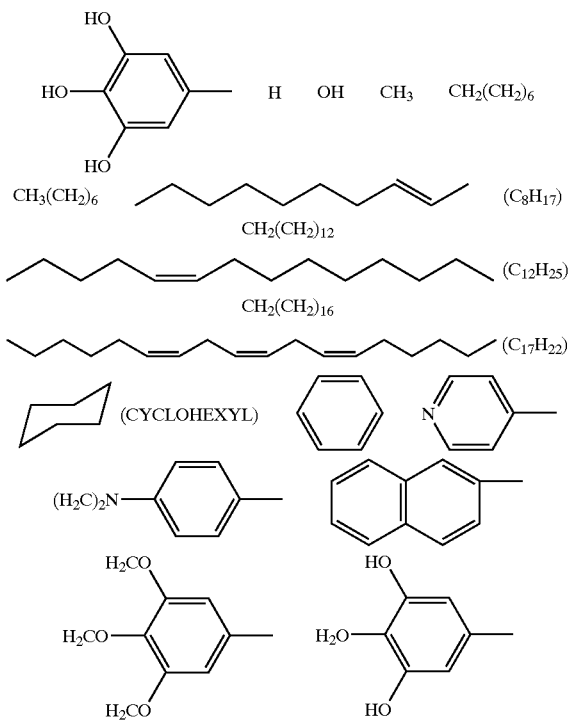

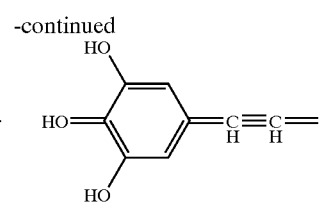

The use of testosterone (or DHT) combinations with the aforementioned 5α-reductase inhibitor compounds are also contemplated. The disclosed 5α-reductase inhibitor compounds may be administered in combination with a therapeutically effective amount of testosterone (or DHT) in a pharmaceutically acceptable carrier in the treatment of the various disorders. In one embodiment, the pharmaceutical composition is a percutaneous dosage form comprising testosterone and EGCG.

BRIEF DESCRIPTION OF THE DRAWINGS

In the drawings, which form a portion of the specification:

FIG. 1 is a list of various flavanoid compounds of the present invention and their corresponding structures.

FIG. 2 is a list of various catechol compounds of the present invention and their corresponding structures.

FIG. 3 is a list of various curcumin and related compounds of the present invention and their corresponding structures.

FIG. 4. is a list of various quinone compounds of the present invention and their corresponding structures.

FIG. 5 is a list of various epigallocatechin derivative compounds of the present invention and their corresponding structures.

FIG. 6 is the generic formula of the epigallocatechin derivatives of the present invention;

FIG. 9 is the generic formula of quinones and catechols useful in the present invention.

FIG. 10 is a list of various fatty acids of the present invention and some of their corresponding structures.

FIG. 11a is a graph of the inhibition of type 1 5α-reductase by EGCG. Initial reaction velocities (V) were determined for testosterone concentrations and as a function of EGCG concentrations: 0 μM (■), 5 μM ( ), and 10 μM (●).

FIG. 11b is a graph of the inhibition of type 1 5α-reductase by EGCG. Initial reaction velocities (V) were determined for NADPH concentrations and as a function of EGCG concentrations: 0 μM (■), 20 μM ( ), and 30 μM (●).

DETAILED DESCRIPTION OF THE INVENTION

All of the compositions and methods disclosed and claimed herein can be made without undue experimentation in light of the present disclosure. While the compositions and methods of this invention are described in terms of preferred embodiments, it will be apparent to those of skill in the art that variations may be applied to the compositions, methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

FIG. 6 includes EGC derivatives having the structure depicted in FIG. 6, wherein R may be a chain with 2 to 20 atoms selected from the group consisting of carbon, oxygen, sulfur, and nitrogen, with or without one to four double bonds and additional hydrogen. These atoms can be in a straight chain or branched form, or in the form of aromatic ring structures, which may have a substitution of one to three carbon, alkyl, or halogenated alkyl, nitro, amino, methylated amino, carboxyl, or hydroxy groups, or halogen atoms.

Figure 7:
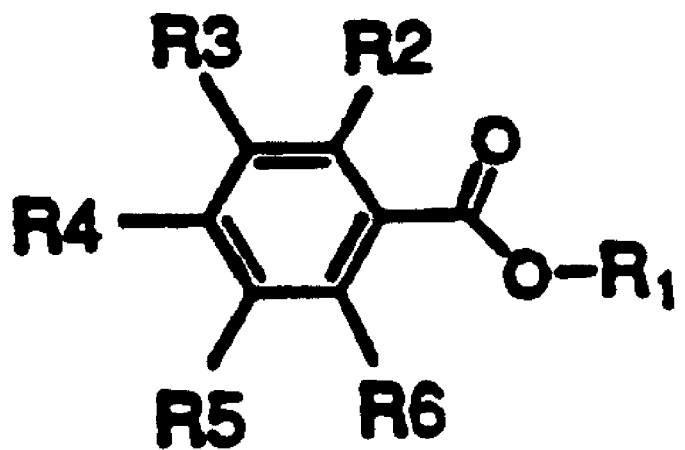
FIG. 7 is the generic formula of gallates useful in the present invention.

FIG. 7 includes several gallate compounds having the structure of FIG. 7 wherein $R_1$ may be an alkyl chain with 2 to 20 atoms selected from the group consisting of carbon, oxygen, sulfur, and nitrogen, with or without one to four double bonds and additional hydrogen. These atoms can be in a straight chain or branched form, or in the form of aromatic ring structures, which may have substitution of one to three carbon alkyl or halogenated alkyl, nitro, amino, methylated amino, carboxyl, hydroxy groups or halogen atoms. $R_2$–$R_5$ may be an alkyl chain with 1 to 12 atoms selected from the group consisting of carbon, oxygen, sulfur, hydrogen and nitrogen, with or without hydroxy groups. These atoms can be in a straight chain or branched form, which may have substitution of one to three carbon alkyl or halogenated alkyl, nitro, amino, methylated amino, carboxyl groups and hydrogen or halogen atoms.

Figure 8:
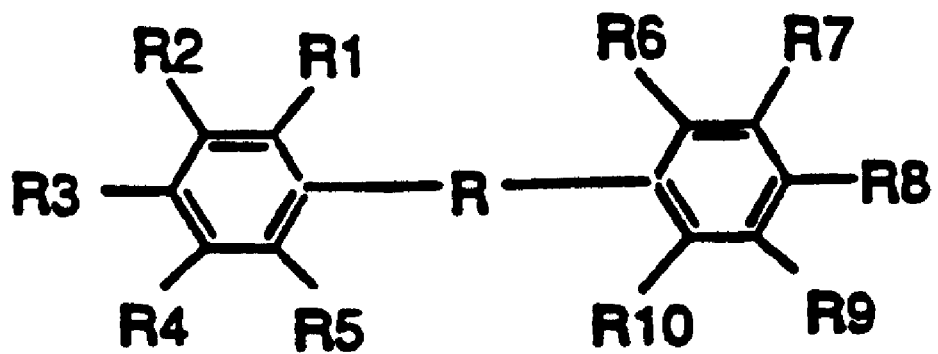
FIG. 8 is the generic formula of curcumin derivatives useful in the present invention.

FIG. 8 includes several curcumin derivatives having the structure of FIG. 8 wherein R may be an alkyl chain with 1 to 14 atoms selected from the group consisting of carbon, oxygen, sulfur, and nitrogen, with or without one to three double bonds, carbonyl, or hydroxyl groups and additional hydrogens. These atoms can be in a straight chain or branched form, or in the form of aromatic ring structures which may have substitution of one to three carbon alkyl or halogenated alkyl, nitro, amino, methylated amino, carboxyl, or halogen atoms. $R_2$–$R_5$ may be hydroxy or methoxy groups or an alkyl chain with 1 to 10 atoms selected from the group consisting of carbon, oxygen, sulfur, hydrogen and nitrogen, with or without hydroxy groups and additional hydrogens. These atoms can be in a straight chain or branched form, which may have substitution of one to three carbon alkyl or halogenated alkyl, nitro, amino, methylated amino, carboxyl groups and hydrogen or halogen atoms.

FIG. 9 includes several quinone and catechol compounds having the structure of FIG. 9 wherein $R_1$–$R_8$ can be 1 to 6 atoms that may consist of carbon, nitrogen, oxygen, and sulfur, and additional hydrogen or halogen atoms. They may be in the form of alkyl or halogenated alkyl, methoxy, nitro, hydroxy or amino groups. $R_9$ and $R_{10}$ may be hydroxy groups or in the form of quinines. Ring B may be in a saturated, aromatic or quinine structure.

The present invention relates to methods of inhibiting 5α-reductase, which include subjecting a cell to an effective concentration of a 5α-reductase inhibitor, such as natural and synthetic flavanoids, catechols, curcumin-related substances, quinones, catechins, particularly epigallocatechin derivatives, fatty acids, and the analogues or derivatives of any of these compounds (FIGS. 1–10).

The present invention also relates to novel compounds. These compounds have the formula:

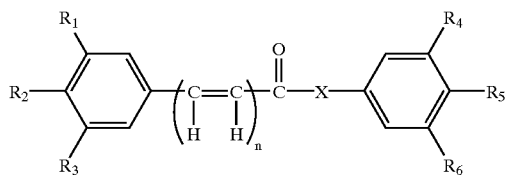

where x is —NHCH$_2$CH$_2$— or —CH=CH—;

$R_1$, $R_2$ and $R_3$ each may be —H, —OH or —OCH$_3$, provided that only one of $R_1$, $R_2$, and $R_3$ may be —H;

$R_4$, $R_5$ and $R_6$ each may be —H, —OH, —OCH$_3$ or —N(CH$_3$)$_2$, provided that only one of $R_4$, $R_5$ and $R_6$ may be —H; and n is 0 or 1.

Further, the novel compounds may be an epigallocatechin derivative having the formula:

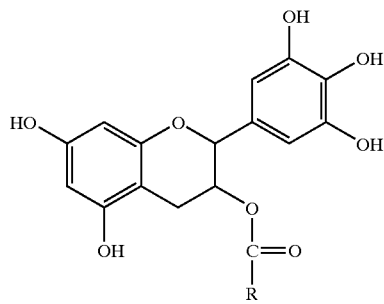

where R is

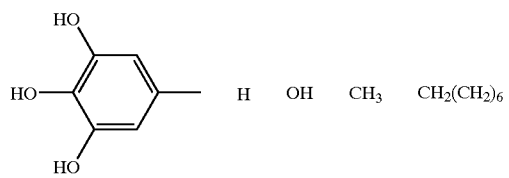

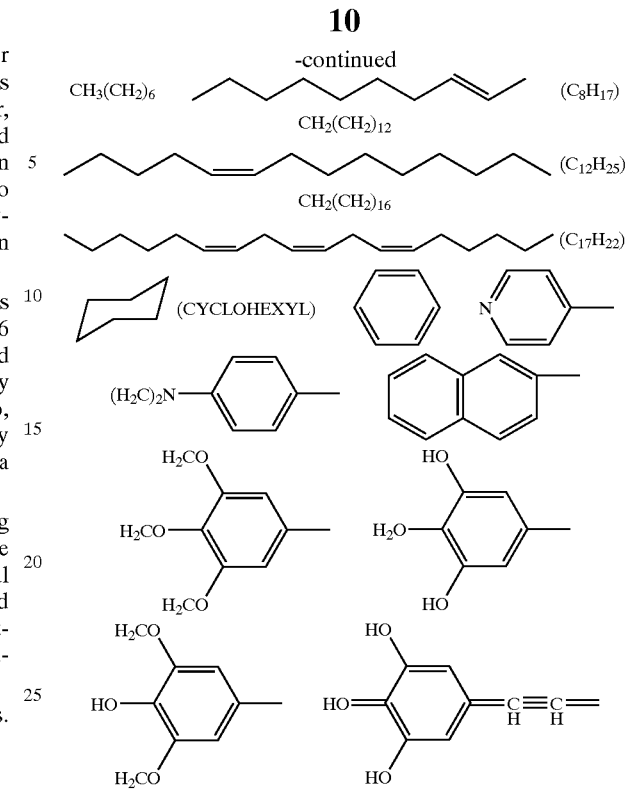

In certain aspects, these compounds are employed to repress excessive androgenic activity by inhibiting the formation and availability of active androgen in target cells. Consequently, the present invention is useful for the treatment of a wide variety of conditions including, but not limited to, the treatment of prostatic hyperplasia, prostatic cancer, breast cancer, skin cancer and other skin diseases, hirsutism, male pattern baldness, seborrhea, obesity, and other diseases related to lipid synthesis, body weight, and/or androgen function, particularly androgen hyperactivity. It is believed that the use of such inhibitors to block abnormal androgen action will serve to treat cancer in conjunction with other agents, chemotherapy, resection, radiation therapy, and the like. The compounds of this invention, besides acting as 5α-reductase inhibitors, may have other effects that can lead to antitumor activity or to suppress abnormal growth of prostate or other organs. Further, several of these compounds have been shown to effectively decrease body weight, and in some cases, to decrease the weight of an androgen-dependent body organ, such as the prostate and other organs.

In mammalian cells, 5α-reductase is very tightly associated with intracellular membranes, including the membrane of the endoplasmic reticulum and contiguous nuclear membranes. Therefore, attempts to solubilize and purify active 5α-reductase have not been very successful. The assay of 5α-reductase activity, therefore, is performed by measuring the rate of conversion of testosterone to 5α-DHT by whole cells or by microsomal and nuclear preparations in the presence of NADPH (enzymatic assay). Alternatively, the 5α-reductase activity can be reliably assayed by following NADPH-dependent non-covalent binding of a potent radioactive inhibitor, such as [$^3$H]4-MA ([$^3$H]4-MA-binding assay), which strongly competes with testosterone for binding to the reductase. The results of the two assays correlate very well when microsomal preparations from different organs or animals are used for comparison.

Further, it has been found that the administration of testosterone may inhibit prostate cancer cell growth.

Therefore, pharmaceutical compositions comprising testosterone in combination with natural and synthetic flavanoids, catechols, curcumin-related substances, quinones, catechins, particularly epigallocatechin derivatives, fatty acids, or the analogues or derivatives of any of these compounds (including but not limited to those listed in FIGS. 1–10) may be useful for regulating 5α-reductase activity. In a broad aspect of the invention, other steroids in the testosterone anabolic or catabolic pathway, may be used, such as, for example, androstenedione, androstenediol, dehydroepiandrosterone, prenenolone, DHT, methyltestosterone, nandrolone, oxymetholone, and their salts, isomers, esters, racemic mixtures, pro-drugs and derivatives. Further, testosterone propionate may also be utilized as the testosterone composition of the present invention.

The method of the present invention also comprises administering to the mammal in a combination therapy an amount of testosterone (or other androgen) and at least one 5α-reductase inhibitor. The phrase "combination therapy" embraces the administration of testosterone and at least one 5α-reductase inhibitor as part of a specific treatment regimen intended to provide a beneficial effect from the co-action of these therapeutic agents for the treatment of androgen-related disorders. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days, weeks, or months depending upon the combination selected).

"Combination therapy" generally is not intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, where each therapeutic agent is administered at a different time, as well as administration of these therapeutic agents, or at least two of the therapeutic agents, in a substantially simultaneous manner. Substantially simultaneous administration can be accomplished, for example, by administering to the subject a single composition, capsule, tablet, cream, gel or solution having a fixed ratio of each therapeutic agent or in multiple, single capsules, tablets, creams, gels or solutions for each of the therapeutic agents. Sequential or substantially simultaneous administration of each therapeutic agent can be effected by any appropriate route including, but not limited to, oral routes, percutaneous routes, intravenous routes, intramuscular routes, and direct absorption through mucous membrane tissues, as discussed herein.

The therapeutic agents can be administered by the same route or by different routes. For example, a first therapeutic agent of the combination selected may be administered orally, while the other therapeutic agent of the combination may be administered percutaneously. Alternatively, for example, all therapeutic agents may be administered orally, or all therapeutic agents may be administered percutaneously, or all therapeutic agents may be administered intravenously, or all therapeutic agents may be administered intramuscularly, or all therapeutic agents can be administered topically. The sequence in which the therapeutic agents are administered is not narrowly critical.

The therapeutic agents of the present invention are usually administered in the form of pharmaceutical compositions. These therapeutic agents can be administered (and are effective) by a variety of routes including oral or other enteral route, rectal, transdermal, subcutaneous, intravenous, intramuscular, and intranasal. Such compositions are prepared in a manner well known in the pharmaceutical arts and comprise at least one therapeutic agent. The therapeutic agents of the present invention may be administered by other non-oral routes, including, for example, percutaneous, transmucosal, implantation, inhalation spray, rectal, vaginal, topical, buccal (for example, sublingual), or parenteral (for example, subcutaneous, intramuscular, intravenous, intraperitoneal, intramedullary and intradermal injections).

When administered, the therapeutic agents of the present invention are administered in pharmaceutically acceptable compositions. The therapeutic agents are used in a "pharmacologically effective amount." This means that the doses or concentrations of the testosterone (or other androgen) and/or the 5α-reductase inhibitor is such that in the composition results in a therapeutic level of drug delivered to a mammal's bloodstream over the duration of therapy that the topical, oral or parenteral forms of the pharmaceutical compositions are to be administered.

Such preparations may routinely contain salts, buffering agents, preservatives, compatible carriers, and optionally other therapeutic ingredients. Suitable buffering agents include: acetic acid and a salt, citric acid and a salt; boric acid and a salt; and phosphoric acid and a salt. Suitable preservatives include benzalkonium chloride; chlorobutanol; parabens and thimerosal.

The present invention also includes methods employing pharmaceutical compositions which contain, as the therapeutic agent, the compounds of the present invention associated with pharmaceutically acceptable carriers. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

In making the compositions of the present invention, the therapeutic agent is usually mixed with an excipient, diluted by an excipient or enclosed within such a carrier which can be in the form of a tablet, capsule, sachet, paper, solution in a vial, or other container. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the present invention can be formulated so as to provide quick, sustained or delayed release of the active ingredient after administration to the patient by employing formulations and procedures known in the art.

When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the therapeutic agent, soft and hard gelatin capsules, suppositories, sterile injectable solutions, and sterile packaged powders.

Tablet forms can include, for example, one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmaceutically compatible carriers. The manufacturing processes may employ one, or a combination of, four established methods: (1) dry mixing; (2) direct compression; (3) milling; and (4) non-aqueous granulation. Lachman et al., *The Theory and Practice of Industrial Pharmacy* (1986). Such tablets may also comprise film coatings, which preferably dissolve upon oral ingestion or upon contact with diluent.

In preparing a formulation, it may be necessary to mill the therapeutic agent to provide the appropriate particle size prior to combining with the other ingredients. If the therapeutic agent is substantially insoluble, it ordinarily is milled to a particle size of less than 200 mesh. If the therapeutic agent is substantially water soluble, the particle size is normally adjusted by milling to provide a substantially uniform distribution in the formulation, for example about 40 mesh. Such solid forms can be manufactured as is well known in the art.

For preparing solid compositions such as tablets the principal therapeutic agent is mixed with a pharmaceutical excipient to form a solid preformulation composition containing a homogeneous mixture of a therapeutic agent of the present invention. When referring to these preformulation therapeutic agents as homogeneous, it is meant that the therapeutic agent is dispersed evenly throughout the composition so that the composition may be readily subdivided into equally effective unit dosage forms such as tablets, pills and capsules. This solid preformulation is then subdivided into unit dosage forms of the type described herein.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

In another embodiment of the present invention, the therapeutic agent is formulated as a transdermal delivery device ("patches"). Such transdermal patches may be used to provide continuous or discontinuous infusion of the compounds of the present invention in controlled amounts. The construction and use of transdermal patches for the delivery of pharmaceutical agents is well known in the art. See, for example, U.S. Pat. No. 5,023,252, issued Jun. 11, 1991. Such patches may be constructed for continuous, pulsatile, or on demand delivery of pharmaceutical agents.

Injectable drug formulations include solutions, suspensions, gels, microspheres and polymeric injectables, and can comprise excipients such as solubility-altering agents (for example, ethanol, propylene glycol and sucrose) and polymers (for example, polycaprylactones and PLGA's).

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The pharmaceutically acceptable carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such a lecithin, by the maintenance of the required particle size in the case of a dispersion and by the use of surfactants. Carrier formulations suitable for oral, subcutaneous, intravenous, intramuscular, etc. can be found in *Remington's, The Science and Practice of Pharmacy*, Meade Publishing Company, Easton, Pa.(2000).

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermic or intravenous fluid or injected at the proposed site of infusion, (see, for example, "Remington's Pharmaceutical Sciences", 15th Edition, pages 1035–1038 and 1570–1580).

In other embodiments, one may desire a topical application of compositions disclosed herein. Such compositions may be formulated in creams, lotions, solutions, gels, pastes, powders, or in solid form depending upon the particular application. The formulation of pharmaceutically acceptable carriers for topical administration is well known to one of skill in the art (see, for example, *Remington's The Science and Practice of Pharmacy* (2000)).

In one embodiment, the pharmaceutical composition may be administered topically in a hydroalcoholic gel. The gel may comprise one or more lower alcohols, such as ethanol or isopropanol; a penetration enhancing agent; a thickener; and water. Additionally, the present invention may optionally include salts, emollients, stabilizers, antimicrobials, fragrances, and propellants.

A "penetration enhancer" is an agent known to accelerate the delivery of the drug through the skin. These agents also have been referred to as accelerants, adjuvants, and absorption promoters, and are collectively referred to herein as "enhancers." This class of agents includes those with diverse mechanisms of action including those which have the function of improving the solubility and diffusibility of the drug, and those which improve percutaneous absorption by changing the ability of the stratum corneum to retain moisture, softening the skin, improving the skin's permeability, acting as penetration assistants or hair-follicle openers or changing the state of the skin such as the boundary layer.

The penetration enhancer of the present invention is a functional derivative of a fatty acid, which includes isosteric modifications of fatty acids or non-acidic derivatives of the carboxylic functional group of a fatty acid or isosteric modifications thereof. In one embodiment, the functional derivative of a fatty acid is an unsaturated alkanoic acid in which the —COOH group is substituted with a functional derivative thereof, such as alcohols, polyols, amides and substituted derivatives thereof. The term "fatty acid" means a fatty acid that has four (4) to twenty-four (24) carbon atoms.

Non-limiting examples of penetration enhancers include C8–C22 fatty acids such as isostearic acid, octanoic acid, and oleic acid; C8–C22 fatty alcohols such as oleyl alcohol and lauryl alcohol; lower alkyl esters of C8–C22 fatty acids such as ethyl oleate, isopropyl myristate, butyl stearate, and methyl laurate; di(lower)alkyl esters of C6–C8 diacids such as diisopropyl adipate; monoglycerides of C8–C22 fatty acids such as glyceryl monolaurate; tetrahydrofurfuryl alcohol polyethylene glycol ether; polyethylene glycol, propylene glycol; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; and terpenes.

The thickeners used herein may include anionic polymers such as polyacrylic acid (CARBOPOL® by B. F. Goodrich Specialty Polymers and Chemicals Division of Cleveland, Ohio), carboxymethylcellulose and the like. Additional thickeners, enhancers and adjuvants may generally be found in *Penetration Enhancers*, CRC Press (1995) *Remington's The Science and Practice of Pharmacy*, (2000), *United States Pharmacopeia/National Formulary*.

When the topical form is used, such delivery is dependent on a number of variables including the time period for which the individual dosage unit is to be used, the flux rate of the testosterone and/or 5α-reductase inhibitor from the gel, surface area of application site, etc. The amount of testosterone and/or 5α-reductase inhibitor necessary can be experimentally determined based on the flux rate of the drug through the gel, and through the skin when used with and without enhancers.

Other delivery systems can include time-release, delayed release or sustained release delivery systems. Such systems can avoid repeated administrations of the therapeutic agents of the present invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di- and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. Nos. 4,748,034 and 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

Use of a long-term sustained release implant may be suitable for treatment of androgen-related disorders in patients who need continuous administration of the compositions of the present invention. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above.

In another embodiment, the therapeutic agents come in the form of kits or packages containing at least one 5α-reductase inhibitor, for example, EGCG, and testosterone. Illustratively, the kits or packages contain at least one 5α-reductase inhibitor and testosterone in amounts sufficient for the proper dosing of the drugs. In another embodiment, the kits contain a 5α-reductase inhibitor in a dosage form suitable for oral administration, for example, a tablet or capsule, and testosterone in a dosage form suitable for topical administration. The therapeutic agents of the present invention can be packaged in the form of kits or packages in which the daily (or other periodic) dosages are arranged for proper sequential or simultaneous administration. The present invention further provides a kit or package containing a plurality of dosage units, adapted for successive daily administration, each dosage unit comprising at least one of the therapeutic agents of the present invention. This drug delivery system can be used to facilitate administering any of the various embodiments of the therapeutic compositions. In one embodiment, the system contains a plurality of dosages to be taken daily via oral administration (as commonly practiced in the oral contraceptive art). In another embodiment, the system contains a plurality of dosages to be administered weekly via transdermal administration (as commonly practiced in the hormone replacement art). In yet another embodiment, the system contains a plurality of dosages to be administered daily, or weekly, or monthly, for example, with at least one therapeutic agent administered orally, and/or at least one therapeutic agent administered intravenously.

The compositions are preferably formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. For example, each solid dosage form (e.g., tablet, powder, capsule) may contain from about 100 mg to about 1 g, more usually 250 mg to 500 mg, of a catechin or other 5α-reductase inhibitor. In one embodiment, epigallocatechin gallate is present in about 0.1% to about 95% weight to weight of the composition. Further, each solid dosage form may contain from about 100 mg to about 1000 mg of testosterone or other androgen. In embodiments of gels, creams, ointments or solutions, the testosterone (or other androgen) may be present in about 0.1% to about 10% weight to weight of the composition, and the catechin (or other 5α-reductase inhibitor) may be present in about 0.1% to about 10% weight to weight of the composition. The percentage of the compositions and preparations may, of course, be varied. The amount of active compounds in such therapeutically useful compositions is such that a suitable dosage form will be obtained.

Upon formulation, solutions will be administered in a manner as is therapeutically effective. Variation of the dose of the compositions disclosed herein, will necessarily depend upon the particular subject, and the nature of the condition(s) being treated. The formulations are easily administered in a variety of dosage forms such as just described. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The therapeutic agents of the present invention may also be administered to a subject in the form of a salt, ester, amide, enantiomer, isomer, tautomer, or prodrug, or derivatives of these compounds.

The present invention is further illustrated by the following formulations, which should not be construed as limiting in any way. The practice of the present invention will employ, unless otherwise indicated, conventional techniques of pharmacology and pharmaceutics, which are within the skill of the art.

Formulation 1: Gel

| SUBSTANCE | AMOUNT (w/w) PER 100 g OF GEL |
| --- | --- |
| Testosterone | 0.5 to 5 g |
| EGCG | 0.1 to 10 g |
| gelling agent | 0.2 to 5 g |
| penetration enhancer | 0.2 to 5 g |
| Ethanol | 50 to 95 g |
| Purified water (qsf) | to 100 g |

Formulation 2: Gel

| SUBSTANCE | AMOUNT (w/w) PER 100 g OF GEL |
| --- | --- |
| Testosterone | 0.5 to 5 g |
| γ-linolenic acid | 0.1 to 10 g |
| gelling agent | 0.2 to 5 g |
| penetration enhancer | 0.2 to 5 g |
| Ethanol | 50 to 95 g |
| Purified water (qsf) | to 100 g |

One skilled in the art will appreciate that the constituents of Formulations 1–2 may be varied in amounts, yet continue to be within the spirit and scope of the present invention.

A therapeutically effective amount of the gel is rubbed onto a given area of skin by the user. The combination of the lipophilic testosterone with the hydroalcoholic gel helps drive the testosterone and the 5α-reductase inhibitor into the outer layers of the skin where it is absorbed and then slowly released into the bloodstream.

The time of administration of a therapeutic agent of the present invention varies depending upon the purpose of the administration.

The foregoing topical testosterone plus catechin (or other 5α-reductase inhibitor) compositions have the further advantage of preventing the conversion of testosterone to dihydrotestosterone (DHT) in the skin where a significant amount of 5α-reductase is present. This is advantageous for treating patients for various conditions in which the serum concentration of DHT is to be controlled or minimized while simultaneously achieving certain serum levels of testosterone.

The following examples illustrate the methods and compositions of the present invention, which should not be construed as limiting in any way.

EXAMPLE 1

Inhibition Of 5α-Reductase Activity by Test Compounds

Two different 5α-reductase isozymes have been characterized in humans, monkeys, rats, and mice. The two isozymes share approximately 50% sequence identity and have different biochemical properties. For example, the type 1 isozyme has a broad basic pH optimum and low affinity for testosterone ($K_m$>1 μM) while the type 2 isozyme has an acidic pH optimum and high affinity for testosterone ($K_m$<10 nM). A structure-activity relationship study was initiated to explore the structural requirements for 5α-reductase activity. Data for this study are summarized in Tables 1–7 and FIGS. 1–11.

A. Materials and Methods

1. Expression of Human 5α-Reductases.

For the preparation of rat 1A cells expressing different types of human 5α-reductases, cDNAs for the human type 1 and 2 5α-reductases were isolated from human prostate λgt11 and PC-3 cell λZAP II cDNA libraries using the published sequence of the 5α-reductases, PCR and standard library screening techniques. The type 1 and 2 cDNAs were subcloned into the retroviral expression vector pMV7 and high titer stocks of virus containing the type 1 and 2 cDNAs were generated using the packaging cells BOSC 23 293. Rat 1A cells were infected with virus and cells containing integrated retrovirus were selected for G418 resistance (Brown and Scott, 1987).

Intact cells containing 5α-reductase, their microsomes, or nuclear preparations can also be used to screen 5α-reductase inhibitors.

2. Assay for 5α-Reductase

Microsomes were prepared from rat 1A cells expressing specific types of human 5α-reductase. An enzymatic assay was performed based on the measurement of 5α-DHT production from testosterone in the presence of microsomes prepared from rat 1A cells containing either the type 1 or type 2 human 5α-reductase. The amount of labeled testosterone and dihydrotestosterone in extracts was determined by thin layer chromatography and scanning on a AMBIS radioanalytic scanner. The percent inhibition of type 1 and type 2 isoenzyme of 5α-reductase by 100 μm of test compound was measured. Further, the concentration of test compound inhibiting the conversion of testosterone to dihydrotestosterone by 50% (IC50) was determined by interpolation between appropriate data points.

The expression of human 5α-reductase isozymes, preparation of cell extracts, and the assay of 5α-reductase is more explicitly detailed in Hiipakka et al., *Biochem. Pharmac.* 63 (2002)

B. Results

The structures of various compounds investigated are shown in FIGS. 1–10.

1. Green Tea Catechins

The green tea catechins, EC, EGC, ECG, and EGCG were tested (Table 1, FIG. 1).

TABLE 1

Inhibition of 5 α-reductase isozymes by green tea catechins[a]

| Catechin | Cell-Free assay IC$_{50}$ ($\mu$M) | | Whole-cell assay IC$_{50}$ ($\mu$M) | |
|---|---|---|---|---|
| | Type 1 | Type 2 | Type 1 | Type 2 |
| EC | >100 (14) | >100 (4) | >100 (0) | >100 (1) |
| EGC | >100 (15) | >100 (3) | >100 (15) | >100 (1) |
| ECG | 11 (100) | 69 (83) | >100 (0) | >100 (0) |
| EGCG | 15 (99) | 74 (74) | >100 (6) | >100 (0) |

[a]IC$_{50}$: concentration ($\mu$M) of compound producing 50% inhibition of 5 α-reductase activity. Values in parentheses are percent inhibition of 5 α-reductase activity in the presence of 100 $\mu$M concentration of the indicated compound.

The tea catechins, ECG and EGCG, had the highest activity of the tested green tea catechins and were better inhibitors of the type 1 than the type 2 isoenzyme of 5α-reductase. The tea catechins epicatechin (EC) and epigallocatechin (EGC) had little activity. Since ECG and EGCG only differ structurally from EC and EGC by the presence of a gallic acid ester on the 3-hydroxyl, the gallate group may be important for the enhanced ability of ECG and EGCG to inhibt 5α-reductase. These green tea catechins had little inhibitory activity against 5α-reductase in whole cells. The lack of activity in whole cells may be due to an inability of these catechins to cross the cell membrane or to enzymatic or non-enzymatic changes in the structure of these catechins in assays using whole-cell cultures. The stability of EGCG in culture medium may be responsible, in large part, for the lower activity of EGCG in the cell culture assay, since the half-life of EGCG in culture medium and phosphate buffer used for whole-cell and cell-free 5α-reductase assays was 9.5±0.5 and 74.7±6.4 min (mean±SEM, N=3), respectively. The stability of EGCG in aqueous solution is highly dependent on pH, and the difference in pH between culture medium (pH 7.5) and the phosphate buffer for cell-free assays (pH 7.0) may be responsible, in part, for this 8-fold difference in stability. The half-life of EGCG in phosphate buffered saline, pH 7.5, was determined to be 21.2±2.0 min.

Certain flavonoids, including EGCG, produce hydrogen peroxide in aqueous solutions at physiological pH, possibly through a superoxide intermediate. To determine if these reactive oxygen species may have some role in inhibition of 5α-reductase by EGCG, catalase (25–250 $\mu$g/mL) or superoxide dismutase (0.5–5 $\mu$g/mL) were added to assay mixtures containing EGCG. However, additional of these enzymes did not affect inhibition of 5α-reductase type 1 or 2 by 20 or 100 $\mu$M EGCG. Therefore, peroxide and superoxide do not appear to be responsible for inhibition of 5α-reductase by EGCG.

A kinetic analysis of the inhibition of type 1 5α-reductase by EGCG was performed using the cell-free assay to determine the mode of inhibition of EGCG. EGCG was a competitive inhibitor of the substrate NADPH and a non-competitive inhibitor of the substrate testosterone based on double-reciprocal plots of the kinetic data (FIGS. 11a and 11b).

2. Epigallocatechin Derivatives

The high inhibitory activity of EGCG in a cell-free assay but low inhibitory activity in the whole cell assay led us to design and synthesize a series of derivatives of EGC to enhance activity in the whole cell assay (Table 2, FIG. 5).

TABLE 2

Inhibition of 5 α-reductase by various EGC derivatives[a]

| | Cell-free assay IC$_{50}$ ($\mu$M) | | Whole-cell assay IC$_{50}$ ($\mu$M) | |
|---|---|---|---|---|
| EGC derivatives | Type 1 | Type 2 | Type 1 | Type 2 |
| 1. EGCG | 12 (99) | 73 (76) | >100 (11) | >100 (5) |
| 2. HZIV 160 | 29 (99) | 76 (96) | 7 (99) | 8 (98) |
| 3. HZIV 134 | 20 (99) | 67 (94) | ND[b] | ND |
| 4. HZIV 92 | 23 (98) | >100 (45) | 64 (94) | 80 (62) |
| 5. HZIV 120 | 23 (99) | 66 (97) | 49 (97) | 57 (96) |
| 6. HZIV 142 | 25 (97) | 63 (93) | 8 (99) | 14 (98) |
| 7. HZIV 68 | 29 (93) | 99 (51) | >100 (40) | >100 (34) |
| 8. HZIV 75 | 29 (97) | >100 (21) | 43 (83) | 62 (72) |
| 9. HZIV 166 | 30 (98) | 78 (74) | 58 (89) | 72 (83) |
| 10. HZIV 63 | 311 (94) | >100 (20) | >100 (12) | >100 (7) |
| 11. HZIV 169 | 47 (90) | >100 (39) | >100 (10) | >100 (0) |
| 12. HZIV 74 | 48 (85) | >100 (24) | ND | ND |
| 13. HZIV 144 | 49 (88) | >100 (38) | >100 (12) | >100 (7) |
| 14. HZIV 168 | 49 (98) | 73 (92) | 28 (93) | 41 (94) |
| 15. HZIV 166 | 59 (95) | 71 (84) | 58 (89) | 72 (83) |
| 16. EGC | 62 (61) | >100 (30) | >100 (15) | >100 (1) |
| 17. HZIV 107 | 98 (52) | >100 (39) | >100 (23) | >100 (2) |
| 18. HZIV 145 | >100 (35) | >100 (8) | >100 (8) | >100 (9) |
| 19. HZIV 148 | >100 (31) | >100 (0) | 42 (90) | 74 (81) |
| 20. HZIV 109 | >100 (17) | >100 (0) | ND | ND |

[a]IC$_{50}$: concentration ($\mu$M) of compound producing 50% inhibition of 5 α-reductase activity. Values in parentheses are percent inhibition of 5 α-reductase activity in the presence of 100 $\mu$M concentration of the indicated compound.
[b]ND: not determined.

To determine what structural features of the gallate group of EGCG were important for inhibitory activity against 5α-reductase, and to determine whether structural changes in or replacement of the gallate group could enhance inhibitory activity in whole cells, a series of EGC derivatives was synthesized and tested using the cell-free and whole-cell assays (Table 2). Modification of the hydroxyl groups of the gallate ester by methylation or replacement of gallic acid with various aromatic groups without phenolic groups did not improve inhibitory activity in either the cell-free or whole-cell assay. The most significant structural change leading to enhanced activity in the whole-cell assay was introduction of an aliphatic acid ester in place of the gallic acid ester of EGCG. EGC derivatives with long-chain aliphatic acids were better inhibitors than derivatives with short-chain aliphatic acids, and derivatives with aliphatic acids with some degree of unsaturation were better inhibitors than EGC derivatives esterified with saturated aliphatic acids. EGC esterified to either γ-linolenic or myristoleic acid were potent inhibitors of both 5α-reductase in whole cells with IC50 values of less than 15 $\mu$M. Methyl and cholesterol esters of γ-linolenic acid were not potent inhibitors of 5α-reductase (IC50>100 $\mu$M) in cell-free and whole-cell assays (data not shown). Therefore, it is likely that the enhanced inhibitory activity of EGC esterified to γ-linolenic acid is due to the combined functionality of this derivative and not simply due to hydrolysis of the ester bond and release of free γ-linolenic acid. Also, cellular morphology, as determined by light microscopy, was not altered when cells were incubated with EGC derivatives containing γ-linolenic or myristoleic acid esters; therefore, inhibition of 5α-reductase in whole cells was not due to gross changes in cell integrity.

3. Flavonoids

A variety of naturally occurring flavonoids with structures related to the tea catechins were also tested (FIG. 1, Table 3).

TABLE 3

Inhibition of 5 α-reductase isozymes by various natural flavonoids[a]

| | 5 α-Reductase | | | |
|---|---|---|---|---|
| | Cell-Free assay IC$_{50}$ (μM) | | Whole-cell assay IC$_{50}$ (μM) | |
| Polyphenol | Type 1 | Type 2 | Type 1 | Type 2 |
| Myricetin | 23 (96) | >100 (31) | >100 (11) | >100 (11) |
| Quercitin | 23 (96) | >100 (14) | >100 (15) | >100 (29) |
| Baicalein | 29 (79) | 99 (51) | >100 (24) | >100 (4) |
| Fisetin | 57 (97) | >100 (4) | >100 (42) | >100 (27) |
| Biochanin A | >100 (50) | 17 (74) | 64 (64) | 5 (93) |
| Daidzein | >100 (3) | 29 (69) | 10 (13) | 7 (89) |
| Kaempferol | >100 (22) | 12 (62) | 79 (60) | 20 (85) |
| Flavone | >100 (20) | >100 (−52) | ND[b] | ND |
| Genistein | >100 (16) | 23 (76) | >100 (22) | 20 (89) |
| Morin | >100 (6) | >100 (33) | ND | ND |
| Alpha-napthoflavone | >100 (6) | >100 (−13) | ND | ND |
| Taxifolin | >100 (5) | >100 (5) | ND | ND |
| Beta-napthoflavone | >100 (3) | >100 (4) | ND | ND |
| Chrysin | >100 (2) | >100 (1) | ND | ND |
| Rutin | >100 (4) | >100 (0) | ND | ND |

[a]IC$_{50}$: concentration (μM) of compound producing 50% inhibition of 5 α-reductase activity. Values in parentheses are percent inhibition of 5 α-reductase activity in the presence of 100 μM concentration of the indicated compound.
[b]ND: not determined.

To determine what other structural attributes were important for inhibition of 5α-reductase by polyphenolic compounds, a variety of natural and synthetic polyphenols were tested for their ability to inhibit 5α-reductase isozymes in both the cell-free and whole-cell assays. Several naturally occurring flavonoids with structures related to the tea catechins were tested (FIG. 2, Table 3). Four flavonoids, myricetin, quercitin, baicalein, and fisetin, had marked (IC50<100 μM) activity and were more active against the type 1 than the type 2 isozyme. The number and position of B-ring hydroxyl groups appear to be important for inhibitory activity against the type 1 5α-reductase. The flavonols quercitin, myricetin and fisetin, with a catechol or pyrogallol configuration in the β-ring (FIG. 2), has greater inhibitory activity against the type 1 isozyme than the flavonols chrysin, kaempferol and morin that lack hydroxyls in a catechol or pyrogallol configuration (Table 3). A comparison of the structures and inhibitory activities of the flavanols EC and EGC and the flavonols myricetin and quercitin highlights the importance of a 2,3-double bond and a 4-keto group in the C-ring for enhanced inhibitory activity. In contrast to quercitin, rutin, the 3-rutinose glycoside of quercitin, was ineffective against either isozyme (IC50>100 μM). The inactivity of rutin compared with quercitin may be due to the presence of the bulky oligosaccharide rutinose causing steric hindrance or to modification of the 3-hydroxy group. Taxifolin, a flavanone that is structurally similar to quercitin but lacking the 2,3-double bond in the C-ring, was ineffective against either isozyme (IC50>100 μM). Biochanin A, kaempferol, genistein, and daidzein were more effective inhibitors of the type 2 than the type 1 isozyme. With the exception of kaempferol, a flavonol with a single β-ring hydroxyl, these type 2 inhibitors are isoflavones with single hydroxyls on the β-ring. The inhibitory effects of biochanin A, genistein, and daidzein on 5α-reductase have been reported previously. When tested for inhibitory activity on whole cells, most flavonoids showed little or no activity against the type 1 isoenzyme, perhaps indicating limited penetration of these polyhydroxy compounds across the cell membrane or enzymatic or non-enzymatic changes in the cell structure of these compounds in assays using whole-cell cultures. In contrast to the results with the type 1 enzyme, four flavonoids, biochanin A, daidzein, genistein, and kaempferol, had significant inhibitory activity against the type 2 isozyme in the whole-cell assay. The most active of these, biochanin A and daidzein, have only two and three free hydroxyl groups, respectively. These flavonoids may be active in whole cells because they may penetrate cells easier than other flavonoids that have more hydroxyl groups. These flavonoids also may be less susceptible to modification in cell cultures.

4. Catechols

5α-reductase inhibition studied with the flavonoids indicated the potential importance of catechol and pyrogallol moieties for high inhibitory activity. Therefore, a series of compounds with catechol groups was surveyed for activity (Table 4, FIG. 2).

TABLE 4

Inhibition of 5 α-reductase by compounds containing catechols[a]

| | 5 α-Reductase | | | |
|---|---|---|---|---|
| | Cell-free assay IC$_{50}$ (μM) | | Whole-cell assay IC$_{50}$ (μM) | |
| Catechol | Type 1 | Type 2 | Type 1 | Type 2 |
| Anthrarobon | 4 (99) | 50 (97) | 6 (91) | >100 (31) |
| Bromopyrogallol red | 7 (98) | 84 (58) | ND[b] | ND |
| Gossypol | 7 (99) | 21 (99) | 7 (100) | 6 (99) |
| Pyrogallol red | 15 (97) | >100 (27) | ND | ND |
| Nordihydro-guaiaretic acid | 19 (99) | 50 (80) | 19 (99) | 22 (99) |
| Caffeic acid phenethyl ester | 26 (97) | >100 (36) | 8 (99) | 7 (98) |
| Octyl gallate | 27 (99) | 58 (90) | 7 (99) | 18 (94) |
| Purpurogallin | 30 (81) | >100 (31) | ND | ND |
| Hydroxydopamine | 42 (69) | >100 (41) | ND | ND |
| Dodecyl gallate | 43 (88) | >100 (36) | 3 (99) | 7 (98) |
| Pyrocatechol violet | 48 (85) | 100 (47) | ND | ND |
| Pyrogallol | 70 (60) | >100 (28) | >100 (7) | >100 (15) |
| Hematoxylin | 83 (59) | >100 (38) | ND | ND |
| HZIV-82 | >100 (43) | >100 (0) | 3 (79) | >100 (15) |
| Cnc | >100 (42) | >100 (−75) | ND | ND |
| HZIV 90 | >100 (23) | >100 (13) | >100 (34) | >100 (14) |
| Caffeic acid | >100 (13) | >100 (8) | ND | ND |
| HZIV 275 | >100 (10) | >100 (6) | ND | ND |
| Esculetin | >100 (7) | >100 (13) | ND | ND |
| Ellagic acid | >100 (7) | >100 (9) | ND | ND |
| Catechol | >100 (5) | >100 (0) | >100 (9) | >100 (3) |
| Methyl gallate | >100 (5) | >100 (3) | >100 (0) | >100 (0) |
| Propyl gallate | >100 (0) | >100 (0) | >100 (5) | >100 (0) |
| Fraxetin | >100 (2) | >100 (8) | ND | ND |

[a]IC$_{50}$: concentration (μM) of compound producing 50% inhibition of 5 α-reductase activity. Values in parentheses are percent inhibition of 5 α-reductase activity in the presence of 100 μM concentration of the indicated compound.
[b]ND: not detennined.

Thirteen of the 24 compounds listed had IC50's below 100 μM. All were more active against the type 1 than type 2 isoenzyme. Six of these compounds, anthrarobin, dodecyl gallate, gossypol, octyl gallate, caffeic acid phenethyl ester and nordihydroguaiaretic acid were active in whole cell assays. Anthrarobin was much more effective against the type 1 than type 2 isoenzyme; whereas, the other five inhibitors were equally effective inhibitors of both isoenzymes. The synthetic compound HZIV 82 showed little activity in the cell-free assay, but was very active in the whole cell assay with specificity for the type 1 isoenzyme.

The difference in the activities of caffeic acid (IC50>100 μM) and caffeic acid phenethyl ester (IC50=25 μM) (Table 4) may be due to the charged sulfate group which may interfere with binding to 5α-reductase, a hydrophobic enzyme, as well as interfere with the transport of this class of molecule across the cell membrane. Gossypol, a potent inhibitor in both whole-cell and cell-free assays, contains two catechol moieties. Both of these groups could be contributing to the inhibitory activity of this compound. The methyl and propyl esters of gallic acid were much less potent inhibitors of 5α-reductase than the octyl and dodecyl esters. The latter are more hydrophobic than the former and may interact more readily with microsomal 5α-reductase because of their hydrophobic nature. Dodecyl and octyl gallate were more potent inhibitors in the whole-cell than in the cell-free assay (Table 4). The long fatty acid esters on dodecyl and octyl gallate may enhance uptake of these compounds in whole cells, and these compounds may concentrate in cell membranes leading to inhibition of 5α-reductase. Hydroxydopamine (3,4,5-trihydroxyphenethylamine), which is structurally similar to the short-chain esters of gallic acid, but is positively charged at a physiological pH, had inhibitory activity in the cell-free assay that was similar in potency to that of dodecyl gallate. The compounds catechol (1,2-dihydroxybenzene), pyrogallol (1,2,3-trihydroxybenzene) and gallic acid (3,4,5-trihydroxybenzoic acid), which have catechols in their structure, had weak inhibitory activity in both cell-free and whole-cell assay systems. Three dyes, bromopyrogallol red (5',5"-dibromopyrogallosulfonephthalein), pyrocatechol violet (pyrocatecholsulfonephthalein) and pyrogallol red (pryrogallolsulfonephthalein), each containing catechol groups, were potent inhibitors of 5α-reductase in the cell-free assay. All three of these dyes are effective inhibitors, even though they contain charged sulfate group. Three naturally occurring catechol-containing compounds, ellagic acid, a condensation product of two gallic acid molecules, and the coumarins, esculetin (6,7-dihydroxycoumarin) and fraxetin (7,8-dihydroxy-6-methoxycoumarin), had little activity (IC50>100 μM) in the cell-free assay.

5. Curcumin and Related Compounds

Curcumin was a very effective inhibitor of either the type 1 or type 2 isoenzyme (Table 5, FIG. 3).

TABLE 5

Inhibition of 5 α-reductase isozymes by curcumin and related compounds[a]

| Compound | 5 α-Reductase | | | |
|---|---|---|---|---|
| | Cell-Free assay IC$_{50}$ (μM) | | Whole-cell assay IC$_{50}$ (μM) | |
| | Type 1 | Type 2 | Type 1 | Type 2 |
| Curcumin | 3 (95) | 5 (87) | 9 (99) | 7 (99) |
| Tetrahydrocurcumin | 80 (56) | 29 (73) | ND[b] | ND |
| Demethoxy-tetrahydrocurcumin | >100 (23) | >100 (42) | ND | ND |
| 4-hydroxy-3-methoxy-cinnamaldehyde | >100 (10) | >100 (−60) | ND | ND |
| Coniferol | >100 (10) | 100 (49) | ND | ND |
| 4-(4-hydroxy-3-methoxyphenol)-3-buten-2-one | >100 (3) | >100 (4) | ND | ND |
| Ferulic Acid | >100 (0) | >100 (18) | ND | ND |
| Capsaicin | >100 (0) | >100 (8) | ND | ND |
| Eugenol | >100 (0) | 100 (50) | ND | ND |

[a]IC$_{50}$: concentration (μM) of compound producing 50% inhibition of 5 α-reductase activity. Values in parentheses are percent inhibition of 5 α-reductase activity in the presence of 100 μM concentration of the indicated compound.
[b]ND: not determined.

Commercially available curcumin was chemically reduced with Pt/H2 and the products, tetrahydrocurcumin and demethoxytetrahydrocurcumin, had much less activity than curcumin. However, tetrahydrocurcumin (HZIV 81-2), which is colorless compared to the bright yellow curcumin, had significant activity in the whole cell assay. The structurally related compounds 4-(4-hydroxy-3-methoxyphenol)-3-buten-2-one, ferulic acid, capsaicin, eugenol and coniferyl alcohol had little inhibitor activity (IC50>100 μM) against either isoenzyme highlighting the importance of the diferulolyl structure for activity against 5α-reductase. Nordihydroguaiaretic acid (NDGA) was also an effective inhibitor of the type 1 (IC50=19 μM) and type 2 (IC50=50 μM) isozymes in cell-free and whole cell assays, but less so than curcumin.

6. Quinones

A variety of quinones were tested for activity against 5α-reductase (Table 6, FIG. 4).

TABLE 6

Inhibition of 5 α-reductase isozymes by quinones[a]

| Quinone | 5 α-Reductase | | | |
|---|---|---|---|---|
| | Cell-Free assay IC$_{50}$ (μM) | | Whole-cell assay IC$_{50}$ (μM) | |
| | Type 1 | Type 2 | Type 1 | Type 2 |
| Purpurin | 2 (95) | >100 (20) | ND[b] | ND |
| Alizarin | 3 (95) | >100 (54) | 6 (75) | >100 (27) |
| Anthrarobin | 4 (99) | 50 (97) | 6 (91) | >100 (31) |
| Menadione | 6 (77) | 5 (81) | 51 (82) | 79 (62) |
| Coenzyme q | 12 (77) | 22 (81) | ND | ND |
| 2,5-dichloroindophenol | 15 (78) | 17 (97) | ND | ND |
| Alizarin red S | 30 (91) | >100 (8) | >100 (22) | >100 (1) |
| Anthrarufin | 40 (67) | >100 (13) | ND | ND |
| Anthraflavic acid | >100 (27) | >100 (22) | ND | ND |
| Quinizarin | >100 (26) | >100 (7) | ND | ND |
| Lapachol | >100 (30) | >100 (9) | ND | ND |
| t-butylhydroxyquinone | >100 (19) | >100 (4) | ND | ND |
| Anthraquinone | >100 (6) | >100 (9) | ND | ND |

[a]IC$_{50}$: concentration (μM) of compound producing 50% inhibition of 5 α-reductase activity. Values in parentheses are percent inhibition of 5 α-reductase activity in the presence of 100 μM concentration of the indicated compound.
[b]ND: not determined.

The naturally occurring anthraquinone, alizarin, was a very effective inhibitor of the type 1 but not type 2 isozymes. Alizarin Red S, which is a water soluble sulfate derivative of alizarin had little activity (IC50>100 μM) against either isoenzyme. The charged sulfate group may prevent interaction with membrane bound 5α-reductase. Purpurin, which has an additional hydroxyl compared to alizarin, had inhibitory activity similar to alizarin. Anthraflavic acid, anthrarufin and quinizarin, which are structural isomers of alizarin without adjacent hydroxyl groups, had much less activity, emphasizing the importance of the catechol moiety for potent inhibitory activity of this class of anthroquinones. Anthraquinone was not an effective inhibitor (IC50>100 μM). Menadione, coenzyme Q, and 2,6dichloroindophenol were potent cell-free inhibitors of both isozymes. The compounds participate in quinone reductase reactions and may deplete NADPH causing the observed inhibition. In the whole cell assay, alizarin was a very effective inhibitor of the type 1 isoenzyme and menadione had moderate activity.

7. Fatty Acids

A variety of fatty acids were tested for activity against 5α-reductase (Table 7, FIG. 10).

TABLE 7

Inhibition of 5 α-reductase isozymes by fatty acids[a]

| | 5 α-Reductase | | | |
|---|---|---|---|---|
| | Cell-Free assay IC$_{50}$ (μM) | | Whole-cell assay IC$_{50}$ (μM) | |
| Fatty Acid | Type 1 | Type 2 | Type 1 | Type 2 |
| Gamma-Linolenic Acid C18:3 CIS 6,9,12 | 5 (99) | 11 (99) | 22 (91) | 20 (86) |
| Crocetin | 7 (70 @ 30) | >100 (20 @ 30) | ND | ND |
| Alpha-Linolenic Acid C18:3 CIS 9,12,15 | 8 (99) | 9 (84) | 29 (82) | 23 (86) |
| Linoleic Acid C18:2 CIS 9,12 | 9 (99) | 19 (85) | 40 (78) | 25 (77) |
| Oleic Acid C18:1 CIS 9 | 10 (99) | 42 (86) | 83 (58) | >100 (45) |
| Conjugated Octadecadienonic Acid | 10 (99) | 30 (81) | ND | ND |
| 5,8,11,14-Eocpsatetraynoic Acid | 15 (97) | 3 (81) | ND | ND |
| Stearic Acid C18:0 | 27 (71) | >100 (35) | >100 (10) | >100 (23) |

[a]IC$_{50}$: concentration (μM) of compound producing 50% inhibition of 5 α-reductase activity. Values in parentheses are percent inhibition of 5 α-reductase activity in the presence of 100 μM concentration of the indicated compound.
[b]ND: not determined.

The greater the degree of unsaturation, the better the inhibitory activity of the fatty acid. Since unsaturated fatty acids are easily prone to oxidation which may comprise their usefulness, we examined some unsaturated fatty acids less prone to oxidation. The synthetic fatty acids, conjugated octadecadienoic acid (CODA) (cis or traps-9,11 or 10,12 octadecadienoic acid) and 5,8,11,14-eicosatetraynoic acid (ETYA), were good inhibitors of both isoenzymes. CODA and ETYA had IC50s of 10 and 15 (type 1) and 30 and 3 (type 2) μM, respectively. The naturally occurring fatty acid, γ-linolenic acid, has IC50 of 3 μM for both isoenzymes. Fatty acids such as ETYA may be useful for derivatizing other 5α-reductase inhibitors to enhance cellular uptake and promote in vivo activity of 5α-reductase inhibitors. Methyl and cholesterol esters of γ-linolenic acid had little activity in the whole cell assay and so the activity of EGC esterified to γ-linolenic acid is unlikely due to intracellular hydrolysis of these esters.

Active 5α-reductase inhibitors shown in Tables 1–7 are polyphenols or their derivatives and are easily oxidized or hydrolyzed within several hours to several days, especially in the presence of air or oxygen and at a pH above 7.0. These compounds are more stable to oxidation or hydrolysis by maintaining the pH of the solutions of these compounds at a pH below 7.0. More than 80% of the oxidation of hydrolysis can be prevented by the addition of an inorganic acid, such as hydrochloric acid, sulfuric acid, or phosphoric acid, or an organic acid, such as citric acid or acetic acid.

C. Discussion

This study identified several natural products that were inhibitors of 5α-reductase. Since some of these compounds were effective on whole cells, they may be capable of modulating the activity of 5α-reductase in vivo.

Many of these compounds were better inhibitors of the type 1 than the type 2 isozyme, while a few inhibited both isozymes equally. Biochanin A, daidzein, genistein, and kaempferol were the only polyphenols tested that were better inhibitors of the type 2 than the type 1 isozyme. The first three compounds are isoflavones, while kaempferol is a flavonol. Since the type 2 isozyme of 5α-reductase has a critical role in prostate development and is the predominant isozyme present in the adult human prostate, pharmaceutical compositions rich in these particular compounds have the potential to affect the development and function of the prostate by modulating the activity of 5α-reductase. Since excessive 5α-reductase activity has been proposed to be a possible contributing fact in prostate cancer development or progression, the development and progression of prostate cancer may also be affected by pharmaceutical compositions containing inhibitors of 5α-reductase. These pharmaceutical compositions may have the ability to act as prostate cancer chemopreventative agents by modulating 5α-reductase activity.

A consistent observation in this study was the polyphenolic inhibitors of the type 1 5α-reductase had a catechol in their structure. Flavonoids that were better inhibitors of the type 2 than the type 1 5α-reductase, however, did not contain catechols. Although a catechol group was necessary for potent inhibition of the type 1 isozyme by polyphenols, it was not always sufficient. For instance, the natural product ellagic acid contains two catechol groups and was a weak (IC50>100 μM) inhibitor of 5α-reductase. The proximity of the catechols in ellagic acid to other molecular groups may have steric effects, and the highly constrained structure of ellagic acid may prevent inter- and intra-molecular interactions necessary for inhibition by catechol-containing compounds.

Inhibition of the type 1 5α-reductase by EGCG, which contains two separate catechol/pryogallol groups in its structure, was competitive with the substrate NADPH. Therefore, the catechol groups in EGCG may be interacting with amino acid residues important for binding of this cofactor by 5α-reductase. Several studies, based upon characterization of naturally occurring mutants, site-directed mutagenesis, and photoaffinity labeling of 5α-reductase, have identified certain amino acid residues that may have a role in substrate and cofactor binding. NADPH-binding is altered by certain amino acid changes in the carboxyl-terminal half of the protein, while substrate (testosterone) or inhibitor (finasteride) binding is affected predominantly by changes in the amino-terminal half of the protein, although some changes in the carboxyl-terminal half also affect binding of substrate. Photoaffinity labeling of the rat type 1 5α-reductase with 2-azido NADP+ modifies a portion of the carboxyl-terminal half of the protein that is conserved among human and rat 5α-reductase isoforms. Since EGCG was a competitive inhibitor of NADPH, it may have inhibited the enzyme by interactions with residues in the carboxyl-terminal portion of the protein. Although the inhibition of 5α-reductase by EGCG was determined to be competitive, inhibition of the type 1 5α-reductase by 100 µM EGCG could not be reversed by pelleting microsomes exposed to EGCG and then resuspending them in new reaction buffer with EGCG. EGCG either must be strongly bound to microsomes or must permanently alter 5α-reductase causing irreversible inhibition. Inhibition of 5α-reductase by EGCG also did not increase when microsomes containing the type 1 or 2 5α-reductase were incubated with EGCG for 15–60 min prior to the start of the assay.

Natural polyphenols, such as EGCG and certain other flavonoids, have been shown to inhibit a variety of enzymes. Three properties of these compounds that may be responsible for the biological activity are their ability to form complexes with certain metal ions, their anti-oxidant and pro-oxidant activities, and their ability for form complexes with proteins. Given our current understanding of the mechanism of 5α-reductase, it does not appear likely that metal ion complexation or anti- or pro-oxidant activity would be responsible for inhibition of 5α-reductase by EGCG and other polyphenols. The tea catechins ECG and EGCG will form precipitates with soybean lipoxygenase and yeast alcohol dehydrogenase. EGCG will rapidly precipitate certain proteins, such as chicken egg white lysozyme. The basis for this precipitation activity has not been defined thoroughly, but it may be due to the ability of certain polyphenols to form both numerous H-bonds with protein, as well as unselective association of the aromatic nuclei of a polyphenol with certain amino acids, especially pralines. Types 1 and 2 human 5α-reductase contain 14 (5.4%) and 17 (6.7%) proline residues, respectively; hence, these enzymes are not proline-rich proteins. Also, only five of these proline residues are in the carboxyl-terminal half of the protein containing the putative NADPH-binding site.

Catechols can form o-quinones, which are known to react covalently with both primary amines and sulfhydryls. EGCG and other green tea catechins react covalently with sulfhydryls. Both the type 1 and 2 5α-reductase are inhibited by sulfhydryl modifying agents, such as N-ethylmaleimide, 5,5'-dithiobis(2-nitrobenzoic acid), 2,2'-bispyridyldisulfide, p-hydroxymercuribenzoate, and mercuric chloride (unpublished observation). However, inclusion of 0.1–10 mM dithiothreitol or β-mercaptoethanol in assays did not prevent inhibition of 5α-reductase of EGCG. Therefore, it is unlikely that EGCG inhibited 5α-reductase by covalently modifying essential sulfhydryl groups.

EXAMPLE 2

Treatment of Prostate Cancer

The disclosed compounds of this invention may also be used to treat prostate cancer. The effectiveness of such compounds against prostate cancer can be determined either on isolated cell lines derived from such cancer tissues or in animals demonstrating prostate cancer.

A. Materials and Methods

By way of example, human prostate cancer PC-3 cells are grown in culture medium. About one million cells are injected into male nude mice and the growth of tumors followed. Within two weeks, the tumor grows to about 100 min$^3$. Three tumor bearing mice are injected with a test compound each day.

EXAMPLE 3

Treatment of Breast Cancer

The disclosed compounds of this invention may be used to treat breast cancer. The effectiveness of such compounds against breast cancer can be determined either on isolated cell lines derived from such cancer tissues or in animals demonstrating breast cancer.

EXAMPLE 4

Organ and Body Weight Loss

The disclosed compounds of this invention may also be used to decrease organ and body weight. The compounds thus have use in treating obesity. The effectiveness of a compound can be determined using well-known animal models.

A. Materials and Methods

By way of example, male Sprague-Dawley rats (body weight 180 g±10 g) are used. Compounds are intraperitoneally injected into rats in one group each day for 7 days. Rats in the control group receive 0.1 ml 30% ethanol. Body and organ weights are determined.

EXAMPLE 5

Treatment of Skin Disorders

An inhibitor of 5α-reductase that would be active topically and inactive systemically would be ideal for treatment of androgen-dependent dermatological disorders. Especially useful in the evaluation of the effects of these compounds on skin cells or sebaceous glands is the hamster flank organ (Frost and Gomez, 1972). The paired flank organs, one on each side of the costovertebral angle, are highly sensitive to androgen stimulation. The androgen sensitive structures in the flank organ include dermal melanocytes, sebaceous glands, and hair follicles (Hamilton and Montagna, 1950). This animal model has been widely used for testing androgenic and antiandrogenic compounds. The unique advantage of this animal model is that a testing compound can be applied topically to only one of the flank organs and the effect observed on both organs. If the test compound has only a local effect, then only the treated flank organ is affected. However, if the effect is systemic, then both flank organs are affected.

A. Materials and Methods

1. Chemicals

Fatty acids were obtained from Sigma Chemical Co. (St. Louis, Mo.). Testosterone and DHT were purchased from Steraloids (Wilton, N.H.). Catechins were isolated from green tea by the procedure described previously (Liao and Hiipakka 1995). Fatty acid esters of EGC, EGC-γ-linoleneate and EGC-3-myristoleate, were synthesized by transesterification of the appropriate methyl ester of EGC (Meth-Cohn 1986). The purity of compounds was determined by thin-layer chromatography or HPLC analysis. To avoid oxidation, all test compounds were dissolved in ethanol, placed in a vial wrapped with aluminum foil, and stored at 4 C. Air in the vials was displaced with nitrogen gas by placing one or two drops of liquid nitrogen into each vial before they were capped. The nitrogen was replaced each time the vials were opened. The purity of the test compounds was over 95%.

2. Animals and Treatment

Prepubertal male Syrian golden hamsters, castrated at 4 weeks of age, were obtained from Harlan Sprague-Dawley Co. (Madison, Wis.). Bilateral orchiectomy was performed under anesthesia. The hamsters were housed individually in plastic cages and had free access to Purina rodent chow and water, and were maintained on a 12-h light/12-h dark cycle. Hamsters were used 1–2 weeks after castration and were divided into groups of 4–6 or 9–11 animals. Hair on the lower back of each animal was shaved weekly with an electric hair clipper to expose the flank organs. A treatment solution (5 µl with ethanol as vehicle) was applied topically to the flank organ once a day using a Pipetteman and a polypropylene disposable tip. The treatment solution contained either (a) ethanol alone, (b) an androgen (testosterone or DHT), (c) a test compound, or (d) a combination of an androgen and a test compound. For each hamster, one flank organ was treated while the other organ was not treated. The surface of the flank organ was wiped with an alcohol pad to remove residual compound before each treatment. At the end of each experiment (18 days), animals were killed by $CO_2$ asphyxiation or an intraperitoneal injection of phenobarbital (65 mg/ml per animal). Flank organs from both the treated and untreated sides were examined 1 day after the last treatment by the methods described below. The body weight of each animal was recorded before and after treatment. Experiments were repeated at least twice to assure reproducibility. The "Guide for the care and use of laboratory animals" (NIH publication no. 85-28, revised 1988) and the regulations of the U.S. Department of Agriculture were followed throughout the experiments.

B. Results

1. Determination of the Area of the Pigmented Macule of Flank Organs and Analysis of Data In this study, the growth of the flank organ was determined by measuring the length of the long axis and the short axis of the pigmented spot (pigmented macule) with a caliper with a digital display (Digimatic; Mitutoyo Corporation, Japan). The surface area (in millimeters squared) of the spot was calculated as the product of the long axis and the short axis (Gomez and Frost 1975). The areas of the pigmented spots after treatment with ethanol alone or with test compound (in ethanol) alone were less than 10% of the areas of the pigmented spots after treatment with testosterone alone. These values were deducted from the experimental values and are compared in Tables 8–10. For each experiment, the means and standard error of the means (SEM) of the areas of the untreated and treated macules were computed separately for each treatment group. Within each experiment, an overall F-test (one way ANOVA) was used to test the null hypothesis that the mean sizes of the treated macules were the same in all groups, and Dunnett's multiple range test was used to examine differences between the treatment groups (i.e., green tea catechin+androgen, fatty acid+androgen, EGC derivative+androgen, or fatty acid derivative+androgen) and the control group (androgen treatment only). The Mann-Whitney test was used to examine differences between DHT-treated and the DHT and EGCG-treated groups. P-values <0.05 were taken as indicating statistical significance in all tests (Hochberg and Tamhane 1987).

Flank organs were treated daily with 5 µl ethanol containing 0.5 µg testosterone (T) or DHT with or without 1 mg catechin for 18 days. Each group comprised four to six castrated male hamsters. At the end of the treatment period, the areas of the pigmented macules were determined and are presented as means±SEM in Table 8.

TABLE 8

Effects of green tea catechins on testosterone- or DHT-stimulated growth of the pigmented macules of hamster flank organs.

| Experiment | Treatment | Pigmented macule area (mm$^2$) | Inhibition (%)[a] | P-value[b] |
|---|---|---|---|---|
| I | T (control) | 13.83 ± 1.43 | — | |
| | T + EC (1 mg) | 8.67 ± 1.08 | 37 | <0.05 |
| | T + EGC (1 mg) | 10.75 ± 0.87 | 22 | <0.05 |
| | T + ECG (1 mg) | 5.75 ± 0.57 | 59 | <0.05 |
| | T + EGCG (1 mg) | 8.25 ± 1.43 | 40 | <0.05 |
| | T + EGCG (2 mg) | 5.62 ± 0.75 | 60 | <0.05 |
| II | DHT (control) | 20.80 ± 1.10 | — | |
| | DHT + EGCG (1 mg) | 0.50 ± 0.26 | 97 | <0.05 |

[a]Percent decrease in area of macules treated with tea catechins compared to the area of androgen-treated macules
[b]Mean area of androgen-treated vs. carechin-treated macules; one-way ANOVA Further, flank organs were treated daily with 5 µl ethanol containing 0.5 µg testosterone (T) with or without 1 mg tea catechins, fatty acid or catechin derivatives for 18 days. Each group comprised four to six castrated male hamsters. At the end of the treatment period, the areas of the pigmented macules were determined and are expressed as means±SEM in Table 9.

TABLE 9

Effects of green tea catechin derivatives and fatty acids, on testosterone-stimulated growth of the pigmented macules of hamster flank organs.

| Treatment | Pigmented macule area (mm$^2$) | Inhibition (%)[a] | P-value[b] |
|---|---|---|---|
| T (control) | 17.40 ± 1.93 | — | |
| T + myristoleic acid (1 mg) | 4.63 ± 0.66 | 73 | <0.05 |
| T + EGC-myristoleate (1 mg) | 5.00 ± 0.42 | 71 | <0.05 |
| T + γ-linolenic acid (1 mg) | 3.15 ± 0.42 | 82 | <0.05 |
| T + EGC-γ-linoleneate acid (1 mg) | 5.50 ± 0.56 | 68 | <0.05 |
| T + EGC (1 mg) | 5.50 ± 0.65 | 68 | <0.05 |
| T + EGCG (1 mg) | 6.25 ± 0.82 | 64 | <0.05 |

[a]Percent decrease in area of macules treated with tea catechins, fatty acid or catechin derivatives compared to the area of androgen-treated macules
[b]Mean area of androgen-treated vs catechin-, fatty acid- or catechin derivative-treated macules; one-way ANOVA Flank organs were treated daily with 5 µl ethanol containing 0.5 µg of testosterone (T) or DHT with or without 1 mg alizarin or curcumin for 18 days. Each group comprised four to six castrated male hamsters. At the end of the treatment period, the areas of the pigmented macules were determined and are expressed as means±SEM as shown in Table 10.

TABLE 10

Effects of alizarin and curcumin on testosterone- or DHT-stimulated growth of the pigmented macules of hamster flank organs.

| Experiment | Treatment | Pigmented macule area (mm$^2$) | Inhibition (%)[a] | P-value[b] |
|---|---|---|---|---|
| I | T (control) | 18.65 ± 0.69 | — | |
| | T + alizarin (1 mg) | 2.40 ± 0.47 | 87 | <0.05 |
| | T + curcumin (1 mg) | 2.40 ± 0.65 | 87 | <0.05 |

TABLE 10-continued

Effects of alizarin and curcumin on testosterone- or DHT-stimulated growth of the pigmented macules of hamster flank organs.

| Experiment | Treatment | Pigmented macule area (mm$^2$) | Inhibition (%)[a] | P-value[b] |
|---|---|---|---|---|
| II | DHT (control) | 13.67 ± 0.96 | — | |
| | DHT + alizarin (1 mg) | 10.00 ± 0.43 | 27 | <0.05 |
| | DHT + curcumin (1 mg) | 9.50 ± 0.21 | 31 | <0.05 |

[a]Percent decrease in area of macules treated with alizarin or curcumin compared to androgen-treated macules
[b]Mean area of androgen-treated vs. alizarin- or curcumin-treated macules; one-way ANOVA 2. Histology The skin containing the flank organ was excised, fixed in 10% formalin, and sectioned along the long axis of the organ. The tissue sections were stained with hematoxylin and eosin for microscopic examination.

3. Stimulation of Hamster Pigmented Macule Growth in Castrates by Androgens

A maximum increase in the area of the pigmented macule of the flank organ of castrated hamsters is achieved when 2–5 μg testosterone is applied daily. The pigmented macules grow linearly from about 1–5 mm$^2$ to about 20–30 mm$^2$ within 2–3 weeks. A similar effect is observed when DHT is applied topically to the flank organs. The testosterone- or DHT-treated flank organs, and not the untreated flank organs, are stimulated and became darker and larger. A submaximal dose of 0.5 μg testosterone or DHT per flank organ per day was chosen since at this dose both androgens stimulated flank organ growth moderately to about 15–20 mm$^2$ and exhibited approximately 50–70% of the maximum stimulation (Tables 8–10).

4. Effects of Catechins on Androgen-dependent Stimulation of Pigmented Macules

Castrated hamsters were divided into groups of four to six animals. The flank organs were treated daily for 18 days with a control solvent (ethanol) or with ethanol containing 0.5 μg testosterone or DHT with or without 1 or 2 mg test compound. EC, EGC, ECG, and EGCG inhibited testosterone-induced growth of the pigmented macules by 20% to 60% (Table 8, FIG. 12). The effect of EGCG was dose-dependent (Table 8). At 1 mg, EGCG also reduced DHT-induced growth of pigmented macules by 97%.

Figure 12A:
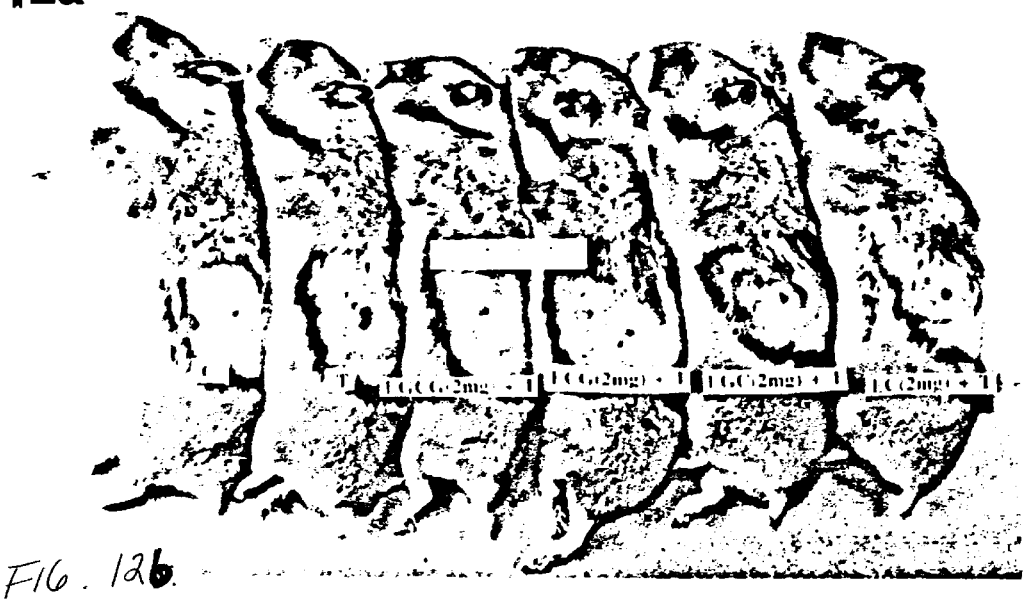
FIG. 12a is a photograph showing androgen stimulation and the effects of tea catechins, alizarin, and curcumin on testosterone-dependent hamster flank organ growth (treatment of left side of castrated male hamsters).
Figure 12B:
FIG. 12b is a photograph showing androgen stimulation and the effects of tea catechins, alizarin, and curcumin on testosterone-dependent hamster flank organ growth (treatment of right side of castrated male hamsters).
Figure 13:
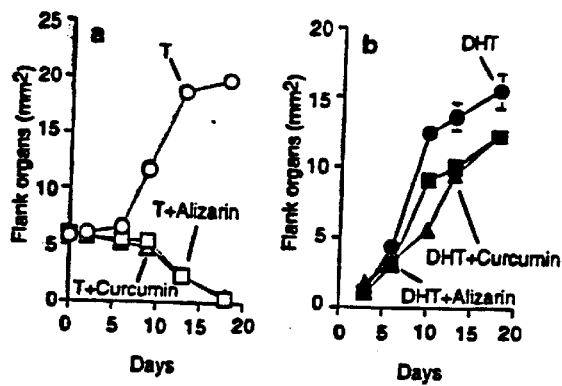
FIG. 13a is a graph depicting the effect of alizarin and curcumin on androgen-dependent growth of pigmented macules of castrated male hamsters where flank organs were topically treated daily with 0.5 μg testosterone (T) alone or with 1 mg alizarin or curcumin for 18 days.
FIG. 13b is a graph depicting the effect of alizarin and curcumin on androgen-dependent growth of pigmented macules of castrated male hamsters where flank organs were treated topically with 0.5 µg DHT alone or with 1 mg alizarin or curcumin daily for 18 days.
Figure 14:
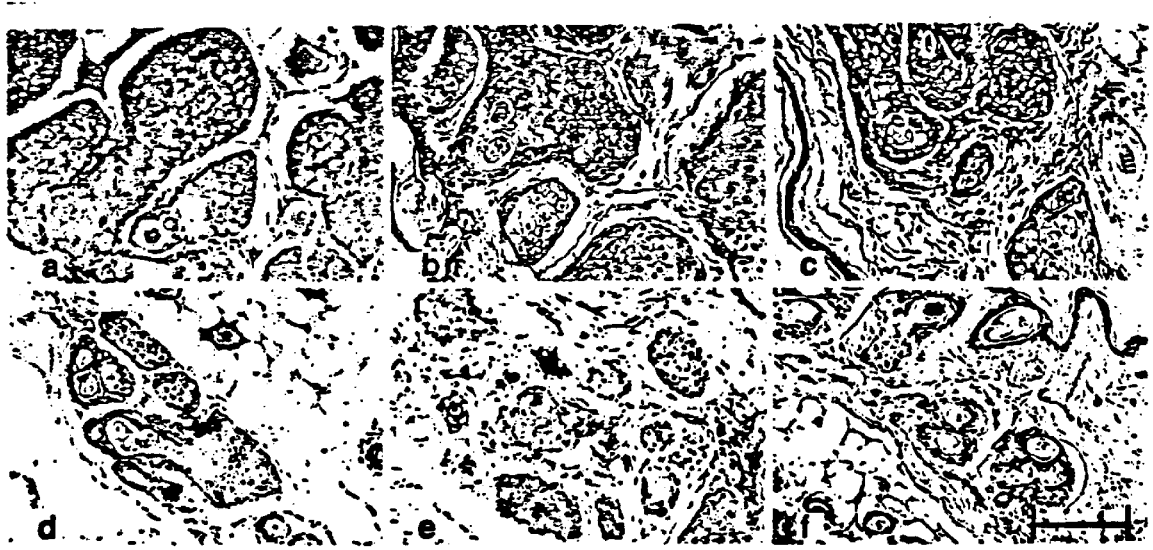
FIG. 14a is a photomicrograph of a hamster flank organ treated topically with testosterone alone.
FIG. 14b is a photomicrograph of a hamster flank organ treated topically with testosterone with 1 mg EC.
FIG. 14c is a photomicrograph of a hamster flank organ treated topically with testosterone with 1 mg EGC.
FIG. 14d is a photomicrograph of a hamster flank organ treated topically with testosterone with 1 mg ECG.
FIG. 14e is a photomicrograph of a hamster flank organ treated topically with testosterone with 1 mg EGCG.
FIG. 14f is a photomicrograph of a hamster flank organ treated topically with testosterone with 2 mg EGCG.

5. Effects of MA, Fatty Acid Esters of EGC, Alizarin, and Curcumin on Androgen-Dependent Stimulation of Pigmented Macules As seen in FIGS. 13a and 13b, flank organs were topically treated daily with 0.5 μg testosterone (T) alone or with 1 mg alizarin or curcumin for 18 days. Flank organs were treated topically with 0.5 μg DHT alone or with 1 mg alizarin or curcumin daily for 18 days. The size of the pigmented macule was measured. Values are means±SEM (n=9–11). Some of the SEM bars in FIG. 12 are too small to be seen.

Both MA and γ-LA, at a dose of 1 mg, inhibited flank organ growth to similar extents. EGC-3 esters of γ-LA and MA also inhibited the growth of flank organs by about 70% (Table 9). Alizarin and curcumin also inhibited the testosterone-dependent growth of flank organs (Table 10, FIGS. 12b and 13a), but they were not as effective in inhibiting DHT-dependent flank organ growth (Table 10, FIG. 13b). Inhibition of androgen-dependent flank organ growth by these compounds and catechins was evident from the fact that the pigmented macules on castrated animals treated with both an inhibitory compound and testosterone were lighter in color and smaller than those on animals treated with testosterone alone (FIG. 12a, b). The contralateral flank organs and the body weights were not affected, suggesting that there was no systemic effect under the experimental conditions.

6. Histological Examination of Catechin Inhibition of Testosterone-Dependent Growth of Sebaceous Glands The effect of tea catechins on the growth of sebaceous glands was examined histologically. The flank organs contained clusters of sebaceous glands. The lobules of the sebaceous glands in the control skin were small and the sebocytes in the lobules stained poorly with eosin. The flank organs from testosterone-treated skin (FIG. 14a) contained distinctly large sebaceous lobules, reflecting an increase in both the number and size of eosinophilic sebocytes in each lobule. The effect of testosterone was reduced considerably by catechin treatment (FIGS. 14b–f). Similar effects were also observed when alizarin and curcumin were used as inhibitors (not shown). Close inspection of pigmented macules revealed that the dark pigment was concentrated at the orifice of hair follicles, rather than distributed in the interfollicular areas of the skin. Histological examination also showed that pigment was localized both in the hair shaft and in the upper dermis around the orifice of hair follicles.

C. Discussion

Four green tea catechins inhibited hamster flank organ growth to various degrees. Like γ-LA (Liang and Liao 1992; Liao and Hiipakka 1995), in an in vitro enzyme assay ECG and EGCG have been shown to be potent inhibitors (IC$_{50}$ 10–20 μM) of the 5α-reductase, while EC and EGC are not active inhibitors of 5α-reductase at 200 μM (Liao and Hiipakka 1995). Consistent with these in vitro tests, EGCG and ECG inhibited the testosterone-dependent growth of flank organs. However, EC and EGC, though inactive against 5α-reductase in vitro, had an inhibitory effect on flank organ growth. The suppression of flank organ growth by catechins, therefore, does not appear to be due simply to inhibition of the formation of DHT from testosterone in flank organs. In line with this observation, EGCG was inhibitory even when DHT instead of testosterone was used as the androgen (Table 8). This is in contrast with γ-LA, which inhibited testosterone-stimulated flank organ growth but not DHT-stimulated flank organ growth (Liang and Liao 1997). Therefore, even though EGCG and ECG can inhibit 5α-reductase, inhibition of flank organ growth by catechins may occur through other mechanisms.

Topically applied γ-LA, however, inhibits flank organ growth in normal hamsters. MA, containing 14 carbons, is as effective as γ-LA in inhibiting flank organ growth. In addition, the effects of MA and γ-LA in preventing testosterone-induced growth of flank organs are similar to the effect of EGC-γ-linoleneate and EGC-myristoleate esters. No differences are noted in the effects of EGCG and that of the synthetic esters which contained γ-LA and MA in place of the gallate group of EGCG.

Alizarin and curcumin may inhibit flank organ growth primarily by inhibiting 5α-reductase. Table 10 shows that alizarin and curcumin inhibited testosterone-induced flank organ growth, but did not curb growth stimulated by DHT. Furthermore, in an in vitro enzyme assay, both compounds have been shown to be potent inhibitors of 5α-reductase (IC$_{50}$ 5–10 μM) (Hiipakka and Liao, unpublished results). These observations support our previous conclusion (Liang and Liao 1997) that flank organ growth is dependent on local conversion of testosterone to DHT as is prostate growth in rodents and humans. Histological observations show that pigments of flank organs were localized in the hair shaft and near the orifice of hair follicles. Therefore, catechins, alizarin, and curcumin inhibit androgenic effects not only in dermal melanocytes, but also in hair follicles of the flank organ.

An inhibitor of a 5α-reductase with systemic activities would be teratogenic to embryos (Imperato-McGinley and Guatier 1986; Russell and Wilson 1994). For this reason a topical preparation of 5α-reductase inhibitor that does not produce systemic activity may be desirable for treating androgen-dependent skin diseases. Since local application of γ-LA and other active compounds did not exhibit a systemic effect on the contralateral flank organs or on prostate organ weights in hamsters, they may be useful for treatment of androgen-dependent skin disorders.

EXAMPLE 6

Topical Effects of Compounds on Hair Loss and Growth

The effects of the topical administration of the compounds of the present invention may be tested on the stumptail macaque monkey. The stumptail macaque monkey develops baldness in a pattern resembling human androgenetic alopecia. The balding process begins shortly after puberty (approximately 4 years of age). This occurs in nearly 100% of the animals, males and females, and is androgen dependent. This is a useful animal model for human androgenetic alopecia and is contemplated to be useful in demonstrating the effects of polyunsaturated fatty acids on hair loss. The following describes a protocol for testing.

A. Materials and Methods

Male stumptail macaques (4 years of age) are divided into groups of 3 to 5 animals. A defined area of the scalp involving the frontal and vertex areas is marked, e.g., by tattoo. Hairs in the marked area are shaved. The solutions of a test compound in different dosages and combinations are evenly applied to the shaved areas once or twice a day. Control animals receive the same volume of the solvent (e.g., ethanol or other organic solvent, or a cream). The same area of the scalp is shaved every 4 to 6 weeks and the weights of hairs shaved are determined. The treatments may last for 6 months to 2 years. 4-MA (17-N,N-diethylcarbamoyl-4-methyl-4-aza-5-androstan-3-one), a 5α-reductase inhibitor known to prevent baldness in this animal is included as a positive control. Biopsies of the scalp (4 mm punch) are obtained before and at the end of the treatments. The specimens are analyzed for 5α-reductase activity and examined histologically for evidence of alopecia.

EXAMPLE 7

Effects of Compounds on Sebum Productions in a Human Model

The effects of the compounds of the present invention on sebum production may also be tested. Topical antiandrogenic activity of several fatty acids and catechins is first evaluated in the hamster flank organ assay or the rat assay. To further confirm the effectiveness of antiandrogenic compounds and suitability for human use, tests are performed on a human male subject. The ideal compounds for human treatment are those that are topically and locally active but do not show systemic antiandrogenic activity, especially in the cases involving young males.

A. Materials and Methods

1. Determination of Forehead Sebum Production

A male volunteer is used to test and analyze sebum production from the forehead region. The forehead is washed thoroughly with soap twice and then cleaned with 70% isopropyl alcohol twice. Sebum production is measured 30 to 60 minutes later with a sebum meter tape probe (7 mm×8 mm) covering 56 mm$^2$ area in each measurement. Ten measurements are made within the 4 cm square area (16 cm$^2$) located at the middle of the left or right side forehead between the eyebrow and the hair line.

The sebum meter detects the difference in the transparency of the tape before and after the tape was placed on the forehead for 30 seconds and expresses the difference in an arbitrary number (S-value) between 0 to 300 (or higher). S-values of sebum accumulated on the foreheads of men are usually 200 to 300. Skin surface on hands usually shows a very low number (5 to 20). The S-value for forehead immediately after washing is less than 5. For men, the S-value gradually increases to about 50 within 30 minutes after washing and reaches 100 to 200 in 45 minutes to 55 minutes.

To determine the rate of sebum production, the left and the right forehead areas are measured alternatively and each time at the comparable areas on the two sides. Ten measurements on each side (i.e., 20 measurements for two sides) take about 15–20 minutes and the sebum-values likely range between 30 to 200. The S-values can differ considerably at different areas of the forehead and could be influenced by environmental, including weather, diet, and physiological, conditions. However, the ratio of the total S-value (the sum of 10 measurements) for the left and the total S-value for the right forehead is constant. Therefore, test compounds applied to the left forehead that reduce the L/R ratio to lower than 1.1 are considered as topically active agents for suppression of sebum production.

EXAMPLE 8

Inhibition of Human Prostate Tumor Growth Using Androgen Compositions

Further, androgen compositions may be administered in the treatment of various androgen-related diseases. To mimic the natural course of human prostate cancer, LNCaP 104-R2 cells were derived from the androgen-dependent LNCaP 104-S cells, after long term culture in androgen-depleted medium (Kokontis et al., 1994). LNCaP 104-R2 cells contain AR but their proliferation is not dependent on androgen. Instead, these cells are proliferatively repressed by very low concentrations of androgen in culture medium. As shown below, testosterone prevents and suppresses the growth of LNCaP 104-R2 tumors in nude mice and this effect is dependent on the conversion of testosterone to 5α-DHT.

A. Materials and Methods

1. Cell Lines

Androgen-dependent LNCaP 104-S (passage 37) and androgen-independent LNCaP 104-R±sublines were isolated as described previously (Kokontis et al., 1994). The characteristics of these cells in vitro were confirmed before injection into nude mice. Briefly, proliferation of LNCaP 104-S cells increased 10–13 fold in media containing 0.1 nM of a synthetic androgen, R1881 compared to cells cultured in media depleted of androgen by charcoal-treatment of the fetal bovine sera (FBS) added to the media. LNCaP 104-R2 cells grew in charcoal-treated media without additional androgen. Their proliferation was not stimulated but was repressed by 0.1 nM R1881. LNCaP 104-S cells were maintained in DMEM (Gibco) supplemented with 1 nM 5α-DHT and 10% FBS (Summit Biotechnology) and LNCaP 104-R2 cells were maintained in DMEM supplemented with 10% FBS treated with charcoal to remove steroid (Kokontis et al., 1994). PC-3 and MCF-7 cell lines were obtained from the American Type Culture Collection (Rockville, Md.), and were maintained in DMEM supplemented with 10% FBS.

2. Animals

BALB/c athymic (nude) male (LNCaP, PC-3 cell lines) and female (MCF-7 cell line) mice (Taconic Inc., Germantown, N.Y.), 5 to 7 weeks-old, were used. Mice were housed in a pathogen-free environment, four to five mice per cage. Cages (filter top), bedding and water were autoclaved before use. Feed was irradiated Pico Lab Mouse Chow 20 5058 (Purina). All procedures involving animals were approved by the University of Chicago Institutional Animal Care and Use Committee. For the tumor growth studies, $10^6$ cells in 0.25 ml of culture medium were mixed with 0.25 ml of Matrigel™ (Collaborative Research, Bedford, Mass.) and were injected subcutaneously into one or both flanks of the mice as described previously (Liao et al., 1995). Tumor size was measured weekly and tumor volume was calculated using the formula L×W×H×0.52 (Janek and Hartman, 1975). Bilateral orchiectomy and subcutaneous implantation or removal of pellets were performed under Metofane anesthesia. Blood samples were obtained by heart puncture or from the orbital plexus while mice were under anesthesia and analyzed for testosterone levels by radioimmunoassay or PSA levels by dual-site reactive enzymatic immunoassay (Tandem®-E PSA, Hybritech, San Diego, Calif.). All steroid hormone (20 mg) pellets were purchased from Hormone Pellet Press (Westwood, Kans.). Finasteride (Proscar®, 5 mg, Merck, N.J.) was obtained from the University of Chicago hospital pharmacy. All numerical data are expressed as the average of the values obtained from 4 to 6 tumors and the standard error.

3. RNA Analysis

Total RNA was isolated from tumor tissue using the acid-guanidium thiocyanate phenol-chloroform extraction method (Chomoczynski and Sacchi, 1987). Ribonuclease protection assay (Zinn et al., 1983; Hay et al., 1987) were performed using probes generated from a 210-bp KpnI-SacI fragment of human AR cDNA (Kokontis et al., 1994; Chang et al., 1988) a 77-bp fragment of human PSA cDNA (Kokontis et al., 1994; Young et al., 1991), a 252-bp PstI-ClaI fragment of human c-myc cDNA (Alitalo et al., 1983) and a 144-bp PstI-HincII fragment at the 5' terminus of human $β_2$-microglobulin (Suggs et al., 1981). Inclusion of a $β_2$-microglobulin antisense RNA probe in hybridizations served as internal standard for normalization of samples containing different levels of total RNA.

4. Sequencing of LNCaP Androgen Receptor mRNA from Tumors cDNA encoding LNCaP AR androgen-binding domain was amplified by RT-PCR™ (Kokontis et al., 1991) using the primers 5'-GGCGATCCTTCACCAATGTC-3' (AR nucleotide sequence number 2780–2799) (SEQ ID NO:1) and 5'-GGAAAGGTCCACGCTCACCAT-3'(AR nucleotide sequence number 3184–3203) (SEQ ID NO:2) (Chang et al., 1988). Gle-purified PCR™ products (424 base pairs) were inserted into the EcoRV site of pBlueScript SK(+) (Stratagene) and sequenced by a double-stranded DNA dideoxy sequencing method using Sequenase (Amersham).

5. Histology and Immunocytochemistry

For histological examination, resected tumor tissues were fixed in 10% formalin, embedded in paraffin, cut into 5 μm sections, and stained with hematoxylin and eosin. Immunolocalization studies on paraffin sections used a rabbit polyclonal anti-human AR antibody (AN-15) (5 μg protein/ml) that is directed against amino acids 1 through 15 of the amino-terminus of AR and polyclonal anti-human PSA antibody (15 μg protein/ml) (DAKO, Carpenteria, Calif.). Nude mice tumors originating from PC-3 cells were used as negative controls. Immunostaining was carried out using a streptavidin-biotin-peroxidase protocol (Liang et al., 1993). For AR immunostaining, deparaffinized tissue sections were pretreated with microwave irradiation in citrate buffer for 5 min. (Hobisch et al., 1995).

6. Abbreviations

AR, androgen receptor; TP, testosterone propionate; R1881, 17 β-hydroxy-17 α-methyl-estra-4,9,11-trien-3-one; DHT, dihydrotestosterone; DMEM, Dulbeccos' Modified Eagle medium; FBS, fetal bovine serum; PSA, prostate specific antigen; RT-PCR™ reverse transcriptase polymerase chain reaction; TGF-β, transforming growth factor-β1.

B. Results

1. Tumorigenicity of LNCaP 104-S and LNCaP 104-R2 Cells in Nude Mice

Palpable tumors were detected in 83% of normal mice, but 0% of castrated mice (Table 12) weeks after injection of LNCaP 104-S cells. In contrast, 5 weeks after injection of LNCaP-R2 cells, palpable tumors were detected in 75% of castrated mice, but 0% of normal mice. However, 7 weeks after injection, palpable LNCaP 104-R2 tumors were detected in 50% of normal mice and their average size was 831±191 (SE) $mm^3$, which was almost the same size as tumors found in castrated mice (884±64 (SE) $mm^3$) at this time. LNCaP cells have a point mutation from A to G (Kokontis et al., 1991; Veldscholte et al., 1990) at nucleotide position 3157 (Chang et al., 1988) in the DNA coding for the androgen-binding domain of AR. It was found that AR cDNA derived from LNCaP 104-S or 104-R2 tumors also have this mutation, which is consistent with these tumors originating from the injected LNCaP cells.

TABLE 11

Tumorigenicity of LNCaP 104-S and LNCaP 104-R in Nude Mice[a] Tumor Incidence

| | LNCaP 104-S | | | | LNCaP 104-R2 | | | |
|---|---|---|---|---|---|---|---|---|
| | Normal | | Castrated | | Normal | | Castrated | |
| Week | No. | % | No. | % | No. | % | No. | % |
| 3 | 0 | (0) | 0 | (0) | 0 | (0) | 0 | (0) |
| 4 | 10 | (83) | 0 | (0) | 0 | (0) | 9 | (0) |
| 5 | 10 | (83) | 0 | (0) | 1 | (0) | 9 | (75) |
| 7 | 10 | (83) | 0 | (0) | 4 | (33) | 9 | (75) |
| 7 | 11 | (91) | 0 | (0) | 6 | (50) | 10 | (83) |

[a]LNCaP cells were injected into 12 normal male nude mice and 12 nude mice castrated 24 hours before cell injection. Mice with palpable tumors were identified every week. No tumors were found three weeks after cancer cell injection. The number of tumor bearing mice is shown under (No.). The percentage of tumor bearing mice is shown in parenthesis.

Figure 15:
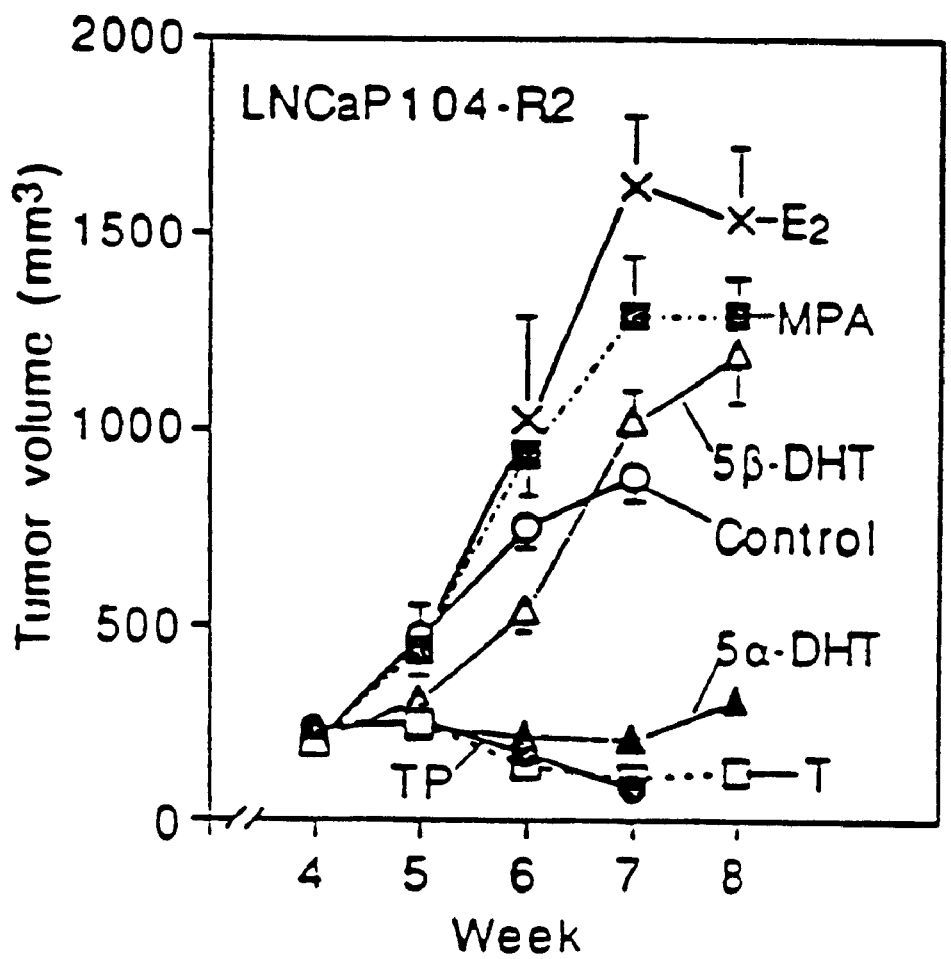
FIG. 15 is a graph of the androgen-specific suppression of the growth of LNCaP 104-R2 tumors in castrated male nude mice. Each point represents data for 6 to 15 tumors.

2. Effect of Androgens and other Steroid Hormones on the Growth of LNCaP 104-R2 Tumors If a testosterone propionate pellet (TP) was implanted at the 4th week in castrated nude mice with growing LNCaP 104-R2 tumors, further tumor growth was inhibited and tumor size was significantly reduced to about 100 mm³ or less at the 7th week (FIG. 15). A similar tumor suppressive effect was observed when testosterone or 5α-dihydrotestosterone pellets were implanted. 5β-dihydrotestosterone, a nonandrogenic stereoisomer of 5α-dihydrotestosterone was not effective, suggesting that the suppressive effect required androgenic steroids. 17β-estradiol and medroxyprogesterone acetate were not suppressive and actually showed some growth stimulatory activity.

3. Effects of Testosterone Propionate on the Growth of Other Tumors

Figure 16:
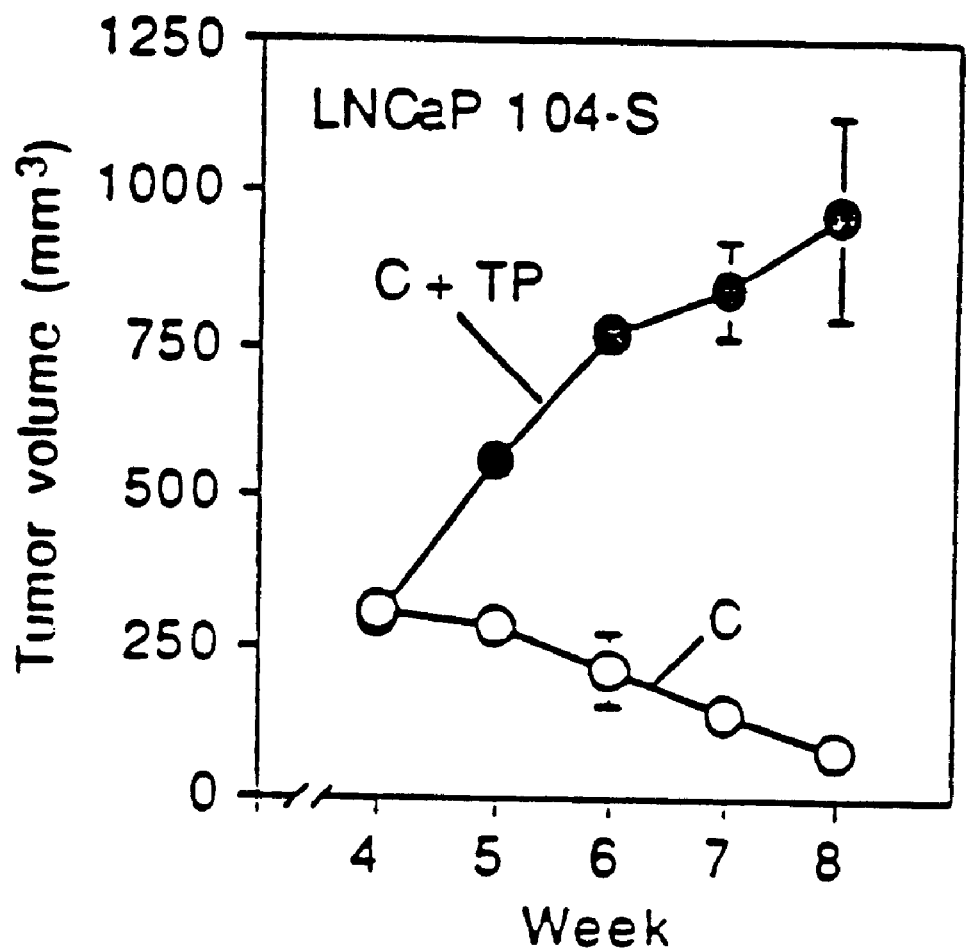
FIG. 16 is a graph of the stimulation of the growth of LNCaP 104-S tumors by testosterone propionate in castrated male nude mice. Each point represents data for 5 tumors.

In contrast to LNCaP 104-R2 tumors, proliferation of LNCaP 104-S tumors was stimulated by androgens (FIG. 16). If tumor bearing nude mice were castrated 4 weeks after injection of cells, growth of LNCaP 104-S tumors stopped and, during the next 4 weeks, tumors regressed to 10% of their size before castration. If TP was implanted at the time of castration, the tumors continued to grow from 299±27 (SE) mm³ to 965±166 (SE) mm³ during the next 4 weeks. TP did not affect the growth of AR negative PC-3 tumors. In female nude mice, the growth of MCF-7 tumors, which express both estrogen and androgen receptors, was also not affected by TP. Therefore, the androgen-dependent suppression of LNCaP 104-R2 tumor growth was both tumor and steroid specific.

Figure 17:
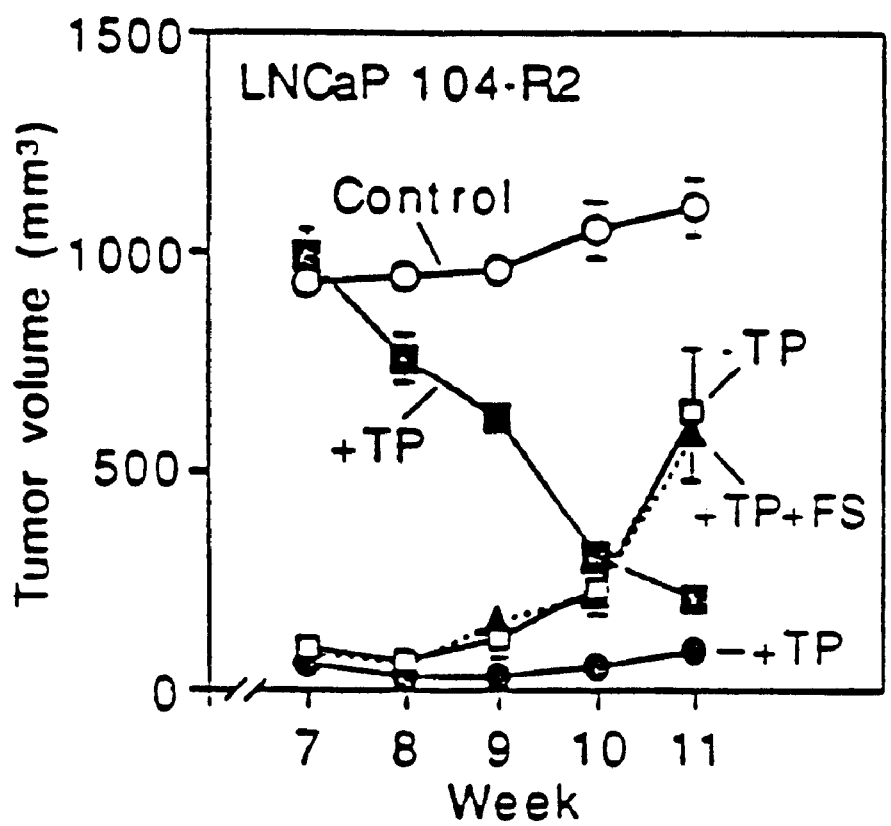
FIG. 17 is a graph of the testosterone-dependent suppression and finasteride-dependent stimulation of the growth of LNCaP 104-R2 tumors in castrated male nude mice (implanted with TP ( ); control ( ); TP implanted at the $4^{th}$ week ( );TP implanted at the $4^{th}$ week and finasteride at the $7^{th}$ week ( ); and mice implanted with TP at the $4^{th}$ week and removed at the $7^{th}$ week ( )).
Figure 18:
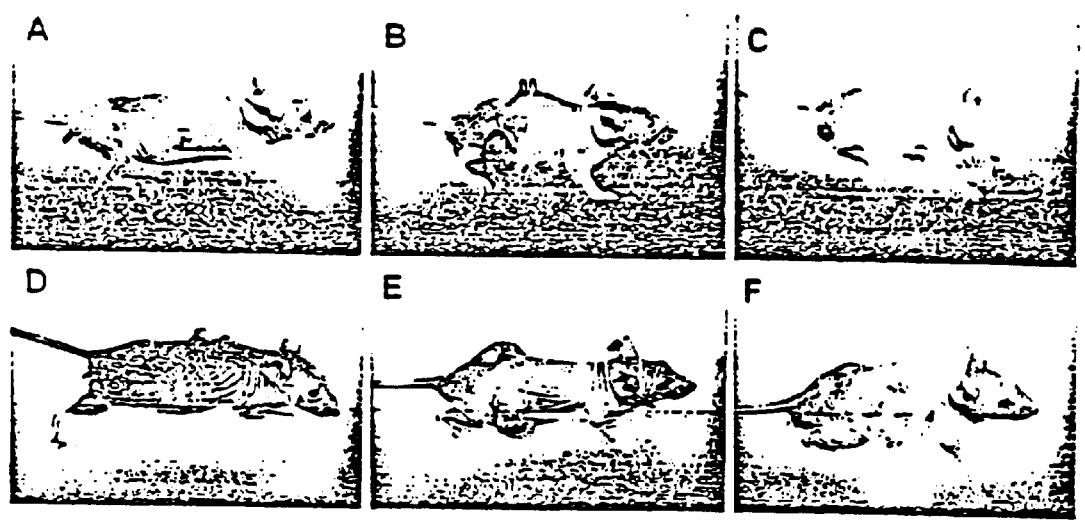
FIG. 18a is a photograph showing the effect of testosterone and finasteride on the growth of LNCaP 104-R2 tumors in castrated male nude mice 7 weeks after injection of LnCaP 104-R2 cells.
FIG. 18b is a photograph showing the effect of testosterone and finasteride on the growth of LNCaP 104-R2 tumors in a castrated male nude mouse with LNCaP 104-R2 tumor as in FIG. 18a and implanted with TP at the $7^{th}$ week and picture taken 1 week later.
FIG. 18c is a photograph showing the effect of testosterone and finasteride on the growth of LNCaP 104-R2 tumors in the mouse in FIG. 18b, 3 weeks later.
FIG. 18d is a photograph showing the effect of testosterone and finasteride on the growth of LNCaP 104-R2 tumors in a castrated male nude mouse of FIG. 18a but implanted with TP at the $4^{th}$ week and picture taken at the $7^{th}$ week.
FIG. 18e is a photograph showing the effect of testosterone and finasteride on the growth of LNCaP 104-R2 tumors in the mouse in FIG. 18d from which TP was removed at the $7^{th}$ week and picture taken 4 weeks later.
FIG. 18f is a photograph showing the effect of testosterone and finasteride on the growth of LNCaP 104-R2 tumors in a castrated male nude mouse treated and the one shown in FIG. 18d and implanted with finasteride at the $7^{th}$ week and picture taken 4 weeks later.

4. Androgen-dependent Remission of LNCaP 104-R2 Tumors and its Reversal by Removal of TP or Implantation of Finasteride The LNCaP 104-R2 tumors in the control castrates grew to 884±64 (SE) mm³ in castrated mice 7 weeks after injection of cells (FIG. 17 and FIG. 18a). TP implantation in these mice resulted in a rapid reduction in tumor size. The effect of TP was clearly visible within one week; massive hemorrhage was seen in tumors (FIG. 18b). Four weeks after TP implantation, tumor size was reduced to 208±33 (SE) mm³ (FIG. 17 and FIG. 18c). If TP was removed at the 7th week from LNCaP 104-R2 tumor bearing mice that were originally implanted with TP at the 4th week (FIG. 15), tumors regrew from 96±26 (SE) mm³ (FIG. 17 and FIG. 18d) to 641±157 (SE) mm³ (FIG. 17 and FIG. 18e) within the next 4 weeks.

5-AR inhibitors (Russell and Wilson, 1994), such as finasteride can prevent testosterone action that is dependent on the conversion of testosterone to 5α-DHT (Bruchosky and Wilson, 1968; Anderson and Liao, 1968). Therefore, the inventors studied whether finasteride can prevent the TP-dependent suppression of LNCaP 104-R2 tumors in nude mice. When finasteride (2.5 mg) pellets were implanted at the 7th week in mice originally implanted with TP at the 4th week, LNCaP 104-R2 tumor growth resumed from the TP repressed level of 84±15 (SE) mm³ and reached 593±144 (SE) mm³ within 4 weeks (FIGS. 17 and 18f). The rate of this regrowth was about the same as that in nude mice from which implanted TP was removed (FIGS. 17 and FIG. 18f). Thus, finasteride alleviated the testosterone suppression of tumor growth.

Figure 19:
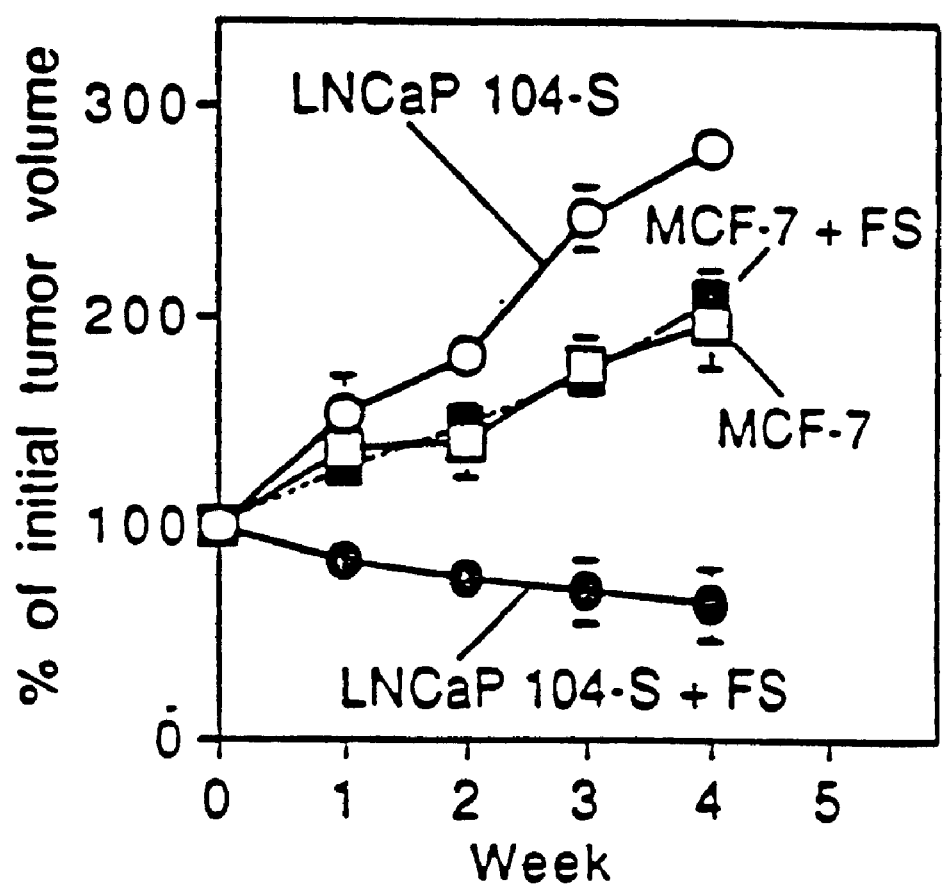
FIG. 19 is a graph of the effect of finasteride on the growth of LNCaP 104-S and MCF-7 tumors in nude mice. Each point represents data for 4 tumors.

In contrast, finasteride treatment of LNCaP 104-S tumors, in normal nude mice, reduced tumor size by 45% from 1,387±432 (SE) mm³ to 759±136 (SE) mnm within 4 weeks (FIG. 19). During this period, the tumor size in the control mice without finasteride implant increased by 240%. Thus 5α-DHT played a major role in maintaining the growth of LNCaP 104-S tumors. Finasteride did not affect the growth of human breast MCF-7 tumors in female nude mice.

5. Histology

Figure 20:
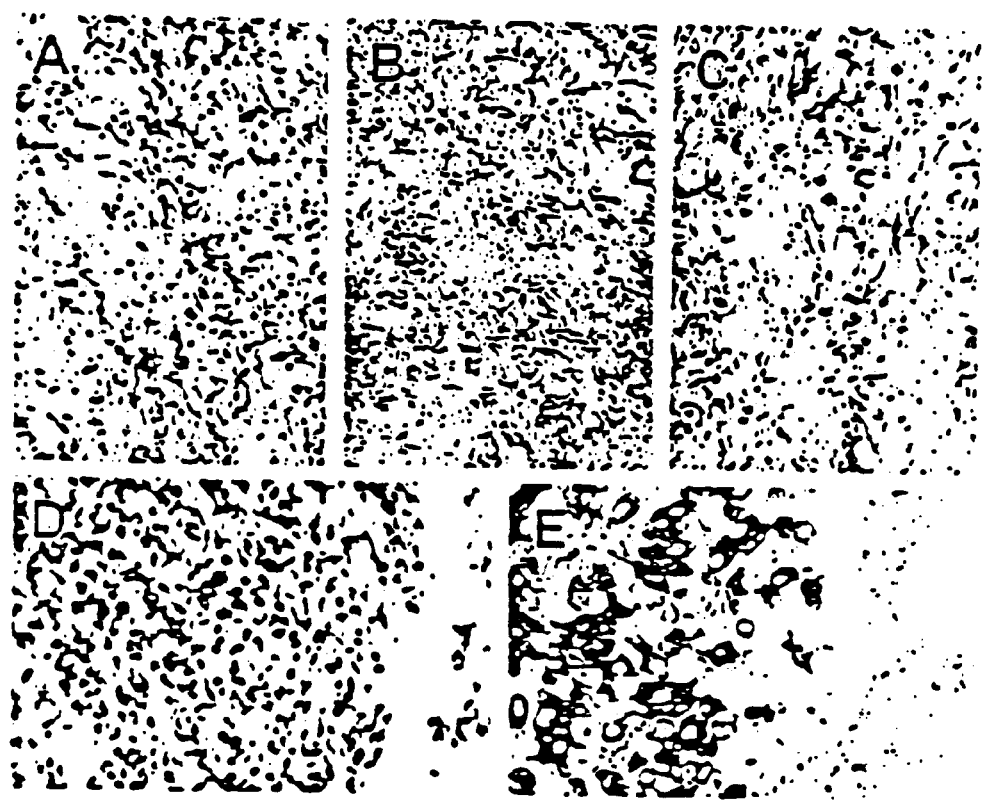
FIG. 20a is a photomicrograph showing the histology of and immunocytochemical localization of androgen receptor and prostate specific antigen (PSA) in LNCaP tumors.
FIG. 20b. is a photomicrograph showing LNCaP 104-R2 tumors from castrated male nude mouse 1 week after implantation of testosterone propionate.
FIG. 20c is a photomicrograph showing LNCaP 104-R2 tumors from a mouse 4 weeks after testosterone propionate implantation.
FIG. 20d is a photomicrograph showing immunocytochemical staining (peroxidase-diaminobenzidine) for androgen receptor in a LNCaP 104-R2 tumor from a castrated male nude mouse.
FIG. 20e is a photomicrograph showing PSA in the LNCaP 104-R2 tumor from a nude mouse implanted with testosterone propionate for 1 week.

There was no clear histological difference between LNCaP 104-R2 and LNCaP 104-S tumors grown in nude mice. For LNCaP 104-R2 tumors, no remarkable histological change was noted within 3 days after TP implantation (FIG. 20a). At 5–7 days after TP implantation, histological sections revealed extensive necrosis with severe hemorrhage (FIG. 20b). At the 4th week after TP treatment, tumor size was markedly decreased, and histological sections revealed fibrosis with infiltration of chronic inflammatory cells and scattered carcinoma cells in the process of degeneration (FIG. 20c).

Figure 21:
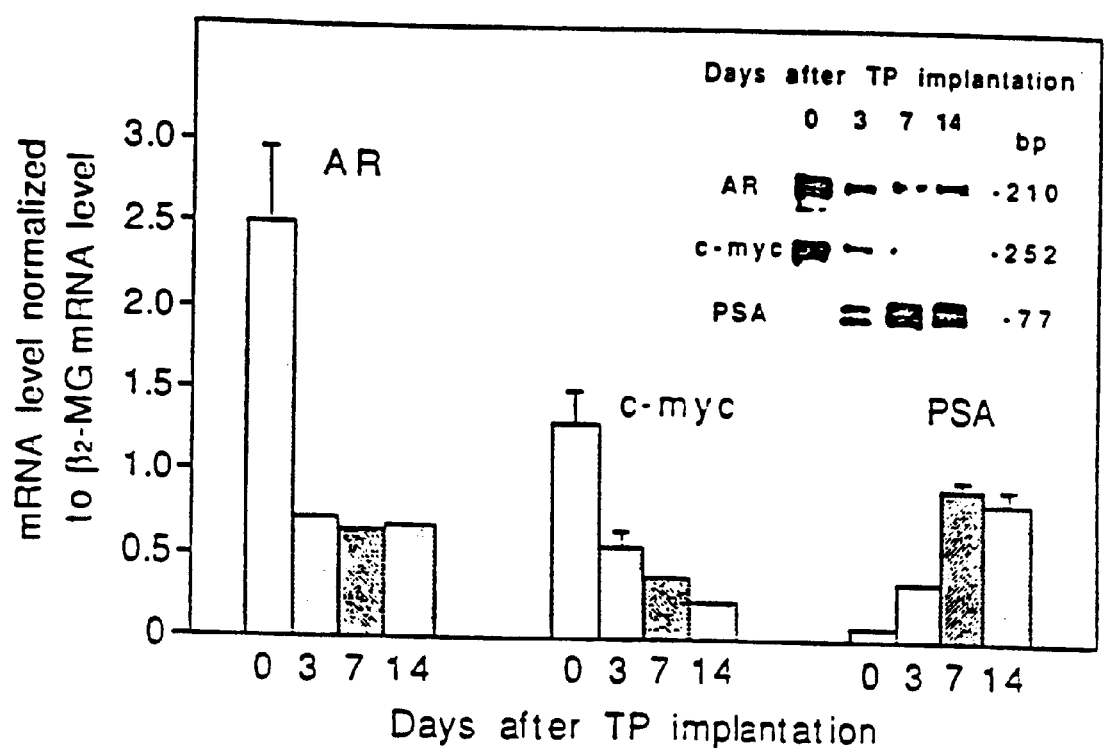
FIG. 21 is a graph of the effect of testosterone propionate on the expression of mRNAs for AR, c-myc, PSA and $\beta_2$-microglobulin in LNCaP 104-R2 tumors.

6. Effect of Androgen on the Expression of Androgen Receptor, c-myc, and PSA by LNCaP 104-R2 Tumors Immunocytochemical staining of LNCaP 104-R2 tumors localized AR to the nucleus (FIG. 20d) and PSA to the cytoplasm (FIG. 20e) in tumor cells but not in surrounding mouse cells. The level of mRNA for AR and c-myc in the LNCaP 104-R2 tumor was reduced by about 50 to 70% within 3 days after TP implantation (FIG. 21). This initial rapid loss preceded the general loss of tumor cells. The level of PSA mRNA in tumor samples (FIG. 21) and serum PSA increased more than 10-fold after 1 week of TP treatment and remained at this high level for at least one more week. At this early stage of TP action, enhanced PSA expression indicates that some tumor cells are viable and still respond to androgenic stimulation.

7. Biological Effects of Androgen in Nude Mice

The results suggest that TP implants were biologically effective for at least 7 weeks. TP used in the studies maintained the serum testosterone level at 20 to 28 ng/ml for at least 7 weeks. In comparison, the serum testosterone level was about 5 ng/ml in normal and 0.3 ng/ml in castrated male mice without TP implants. Since TP stimulated the growth of tumors derived from LNCaP 104-S cells and had no effect on the growth of PC-3 and MCF-7 tumors in nude mice, it is unlikely that the growth suppression of LNCaP 104-R2 tumor by TP was due to a general toxicity of implanted androgen. This conclusion is supported by the fact that at the 4th week after androgen implantation, the seminal vesicle weight in the nude mice with either LNCaP 104-S or 104-R2 tumors increased about 10 times (compared to that in castrates without TP treatment) and there was no loss in the body weight of these nude mice.

C. Discussion

Androgens are necessary for normal prostate development and function. Most newly diagnosed prostate cancers are also androgen dependent. However, the human prostate cancer cells lines, LNCaP 104-R1 (Liao, et al., 1995) and 104-R2 cells±, which contain a very high level of AR (over 10-fold more than the androgen stimulatory LNCaP 104-S cells), are not proliferatively stimulated by androgen but are actually repressed by low concentrations (0.1 nM) of androgens. It has been reported that the proliferation of PC-3 cells transfected with an AR expression vector also is inhibited by androgen in culture (Yuan et al., 1993). It was found that PC-3 cells retrovirally infected with an AR expression vector do not survive well in culture.

Since androgens inhibited the growth of LNCaP 104-R cells in culture (Kokontis, et al., 1994), androgen may exert its effect directly on the tumor cells in nude mice. Excessive expression of androgen-induced gene(s) may result in an imbalance in coordination of various cellular functions or a change in the production of factors that affect cell cycling or apoptosis. For example, TGF-β1 mRNA level in the rat ventral prostate is negatively controlled by androgen (Kyprianou and Issacs, 1989), whereas inhibition of LNCaP cell proliferation by TGF-β1 in culture (Wilding, 1994) is dependent on the presence of an appropriate concentration of androgen (Kim et al., 1996). Androgen also suppresses the expression of prostatic sulfated glycoprotein-2 (Clusterin) (Bettuzzi et al., 1989; Monpetit et al., 1986), which prevents LNCaP cell death induced by tumor necrosis factor α (Sensibar et al., 1995). Tumor growth is dependent on tumor angiogensis (Weidner et al., 1993). However, histological analysis did not reveal a clear effect of testosterone on vascularization in the LNCaP 104-R2 tumor during the initial weeks of tumor growth suppression.

Androgen-repressed LNCaP 104-R2 tumors slowly adapted to growth in the presence of androgens. In normal male mice, LNCaP 104-R2 cells did not grow into palpable tumors in 4 weeks. However, in 50% of these mice, they slowly adapted to the presence of androgen over a 7 week period and grew to a size equivalent to LNCaP 104-R2 cells grown in castrated nude mice for 7 weeks (Table 11). It has been suggested that intermittent use of androgen may delay prostate cancer cell progression (Goldenberg et al., 1995). These observations indicated that some prostate tumors that would be considered androgen-independent may revert to an androgen-sensitive phenotype. These tumors may then be responsive to androgen-ablation therapy.

The derivation of LNCaP 104-R2 cells from LNCaP 104-S cells after a long period (2 years) of culture in androgen-depleted culture medium may mimic the situation in prostate cancer patients who receive androgen ablation therapy (orchiectomy or chemical castration) (Dawson and Vogelzang, 1994; Coffey, 1993; Geller, 1993). Prostatic tumors in these patients initially respond to androgen ablation therapy, but prostate cancer often reappears as an androgen-independent cancer. A recent report showed that distant metastases in patients with prostatic carcinoma who have undergone various kinds of endocrine therapy contain AR (Hobisch et al., 1995). Some of these metastatic prostate tumor cells may behave like LNCaP 104-R2 cells and respond to androgen-suppression or revert to androgen-dependent tumors as shown in the present study.

The 5-AR inhibitor, finasteride, has been found to be effective in the treatment of benign prostatic hyperplasia in some patients (Stone and Finasteride Study Group, 1994). Finasteride is also being tested for the chemoprevention of prostate cancer (Gomley et al., 1995). The present findings indicate that testosterone-suppression of LNCaP 104-R2 tumor growth required conversion of testosterone to 5α-DHT and that finasteride reversed this suppressive effect and promoted the regrowth of LNCaP 104-R2 tumors. It is, therefore, important to consider this adverse effect, if finasteride is to be used in prostate cancer chemotherapy. Flutamide (an antiandrogen being used for prostate cancer therapy) stimulates the growth of LNCaP cells (Wilding et al., 1989) because the AR in these cells has a point mutation in the ligand-binding domain and can utilize antiandrogenic hydroxyflutamide as an androgen to transactivate target genes (Kokontis et al., 1991; Veldscholte, et al., 1990). Effective use of antiandrogens and 5-AR inhibitors for prostate cancer therapy, therefore, needs careful assessment of the particular type of prostate cancer cells present.

LNCaP 104-R (Kokontis et al., 1994) is now designated as LNCaP 104-R1. LNCaP 104-R1 cells were derived from androgen-dependent LNCaP 104-S cells after 40 passages in DMEM containing charcoal-stripped FBS, whereas LNCaP 104-R2 cells were derived from LNCaP 104-R1 cells after 60 additional passages in the same androgen-depleted medium.

All cited literature and patent references are hereby incorporated herein by reference.

What is claimed is:

1. A pharmaceutical composition, comprising: a pharmacologically effective amount of at least one 5α-reductase inhibitor composition in a pharmaceutically acceptable vehicle.

2. The composition of claim 1, wherein the at least one 5α-reductase inhibitor is selected from the group consisting of flavanoids, catechols, curcumin-related substances, quinones, epigallocatechin derivatives, and fatty acids and their analogues or derivatives.

3. The composition of claim 2, wherein the flavanoid is selected from the group consisting of epicatechin gallate, epigallocatechin gallate, myricetin, quercitin, baicalein, and fisetin.

4. The composition of claim 2, wherein the catechol is selected from the group consisting of anthrarobin, bromopyrogallol red, gossypol, pyrogallol red, nordihydrogaiaretic acid, dodecyl gallate, caffeic acid phenethyl ester, and octyl gallate.

5. The composition of claim 2, wherein the curcumin-related substance is selected from the group consisting of curcumin and tetrahydrocurcumin.

6. The composition of claim 2, wherein the quinone is selected from the group consisting of purpurin, alizarin, and anthrarobin.

7. The composition of claim 2, wherein the epigallocatechin derivative is selected from the group consisting of HZIV 160, HZIV 134, HZIV 92, HZIV 120, HZIV 142, HZIV 68, HZIV 75, HZIV 82 and HZIV 166.

8. The composition of claim 2, wherein the fatty acid is selected from the group consisting of γ-linolenic acid, crocetin, α-linolenic acid, linoleic acid, oleic acid, conjugated octadecadienoic acid, 5,8,11,14-eocpsatertraynoic acid, and stearic acid.

9. The composition of claim 3, wherein the flavanoid comprises epigallocatechin gallate.

10. The composition of claim 9, wherein the epigallocatechin gallate is present in an amount from about 0.1 g to about 10 g.

11. The composition of claim 10, wherein the epigallocatechin gallate is present in an amount from about 100 mg to about 1000 mg.

12. The composition of claim 1, wherein the composition is in a dosage form selected from the group consisting of tablet, pill, suspension tablet, powder, lozenge, sachet, cachet, elixir, suspension, emulsion, solution, syrup, aerosol, ointment, soft gelatin capsule, and hard gelatin capsule, suppository, creams, lotions, solutions, gels, and pastes.

13. The composition of claim 12, wherein the solution comprises a sterile injectable solution.

14. The composition of claim 12, wherein the dosage form is further selected from the group consisting of immediate release, sustained release, and delayed release.

15. The composition of claim 12, further comprising an agent selected from the group consisting of an excipient, a lubricant, a wetting agent, an emulsifier, a penetration enhancer, a suspending agent, a preservative, and a flavoring agent.

16. The composition of claim 15, wherein the excipient comprises lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, or methyl cellulose.

17. The composition of claim 16, wherein the lubricant comprises talc, magnesium stearate, or mineral oil.

18. The composition of claim 15, wherein the penetration enhancer comprises isostearic acid, octanoic acid, oleic acid, oleyl alcohol, lauryl alcohol, ethyl oleate, isopropyl myristate, butyl stearate, methyl laurate, diisopropyl adipate, glyceryl monolaurate, tetrahydrofurfuryl alcohol polyethylene glycol ether, polyethylene glycol, propylene glycol, 2-(2-ethoxyethoxy)ethanol, diethylene glycol monomethyl ether, alkylaryl ethers of polyethylene oxide, polyethylene oxide monomethyl ethers, polyethylene oxide dimethyl ethers, dimethyl sulfoxide, glycerol, ethyl acetate, acetoacetic ester, N-alkylpyrrolidone, or terpenes.

19. The composition of claim 1, wherein the 5α-reducatase inhibitor comprises its salt, ester, amide, enantiomer, isomer, tautomer, or prodrug forms.

20. The composition of claim 12, wherein the dosage form is a tablet, suspension tablet, pill, lozenge, sachet, cachet or capsule comprising about 0.1% to about 95% epigallocatechin gallate weight to weight of the composition.

21. A pharmaceutical composition, comprising: a pharmacologically effective amount of of at least one 5α-reductase inhibitor composition and a pharmacologically effective amount of a testosterone composition in a pharmaceutically acceptable vehicle.

22. The composition of claim 21, wherein the at least one 5α-reductase inhibitor is selected from the group consisting of flavanoids, catechols, curcumin-related substances, quinones, epigallocatechin derivatives, and fatty acids and their analogues or derivatives.

23. The composition of claim 22, wherein the flavanoid is selected from the group consisting of epicatechin gallate, epigallocatechin gallate, myricetin, quercitin, baicalein, and fisetin.

24. The composition of claim 22, wherein the catechol is selected from the group consisting of anthrarobin, bromopyrogallol red, gossypol, pyrogallol red, nordihydrogaiaretic acid, dodecyl gallate, caffeic acid phenethyl ester, and octyl gallate.

25. The composition of claim 22, wherein the curcumin-related substance is selected from the group consisting of curcumin and tetrahydrocurcumin.

26. The composition of claim 22, wherein the quinone is selected from the group consisting of purpurin, alizarin, and anthrarobin.

27. The composition of claim 22, wherein the epigallocatechin derivative is selected from the group consisting of HZIV 160, HZIV 134, HZIV 92, HZIV 120, HZIV 142, HZIV 68, HZIV 75, HZIV 82 and HZIV 166.

28. The composition of claim 22, wherein the fatty acid is selected from the group consisting of γ-linolenic acid, crocetin, α-linolenic acid, linoleic acid, oleic acid, conjugated octadecadienoic acid, 5,8,11,14-eocpsatertraynoic acid, and stearic acid.

29. The composition of claim 23, wherein the flavanoid comprises epigallocatechin gallate.

30. The composition of claim 29, wherein the epigallocatechin gallate is present in an amount from about 0.1 g to about 10 g.

31. The composition of claim 30, wherein the epigallocatechin gallate is present in an amount from about 100 mg to about 1000 mg.

32. The composition of claim 21, wherein the at least one 5α-reductase composition is in a dosage form selected from the group consisting of tablet, pill, suspension tablet, powder, lozenge, sachet, cachet, elixir, suspension, emulsion, solution, syrup, aerosol, ointment, soft gelatin capsule, and hard gelatin capsule, suppository, creams, lotions, solutions, gels, and pastes.

33. The composition of claim 32, wherein the solution comprises a sterile injectable solution.

34. The composition of claim 32, wherein the dosage form is further selected from the group consisting of immediate release, sustained release, and delayed release.

35. The composition of claim 32, further comprising an agent selected from the group consisting of an excipient, a lubricant, a wetting agent, an emulsifier, a penetration enhancer, a suspending agent, a preservative, and a flavoring agent.

36. The composition of claim 35, wherein the excipient comprises lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, or methyl cellulose.

37. The composition of claim 36, wherein the lubricant comprises talc, magnesium stearate, or mineral oil.

38. The composition of claim 35, wherein the penetration enhancer comprises isostearic acid, octanoic acid, oleic acid, oleyl alcohol, lauryl alcohol, ethyl oleate, isopropyl myristate, butyl stearate, methyl laurate, diisopropyl adipate, glyceryl monolaurate, tetrahydrofurfuryl alcohol polyethylene glycol ether, polyethylene glycol, propylene glycol, 2-(2-ethoxyethoxy)ethanol, diethylene glycol monomethyl ether, alkylaryl ethers of polyethylene oxide, polyethylene oxide monomethyl ethers, polyethylene oxide dimethyl ethers, dimethyl sulfoxide, glycerol, ethyl acetate, acetoacetic ester, N-alkylpyrrolidone, or terpenes.

39. The composition of claim 21, wherein the 5α-reducatase inhibitor comprises its salt, ester, amide, enantiomer, isomer, tautomer, or prodrug forms.

40. The composition of claim 32, wherein the dosage form is a tablet, suspension tablet, pill, lozenge, sachet, cachet or capsule comprising about 0.1% to about 95% epigallocatechin gallate weight to weight of the composition.

41. The composition of claim 21, wherein said testosterone composition comprises at least one of testosterone, drostenedione, androstenediol, dehydroepiandrosterone, prenenolone, DHT, methyltestosterone, nandrolone, oxymetholone, and testosterone propionate.

42. The composition of claim 41, wherein said testosterone composition comprises testosterone propionate.

43. The composition of claim 21, wherein said testosterone composition is present in an amount from about 0.1 mg to about 10 mg.

44. The composition of claim 43, wherein said testosterone composition is present in an amount from about 0.5 mg to about 5 mg.

45. The composition of claim 21, wherein the testosterone composition is in a dosage form selected from the group consisting of tablet, pill, suspension tablet, powder, lozenge, sachet, cachet, elixir, suspension, emulsion, solution, syrup, aerosol, ointment, soft gelatin capsule, and hard gelatin capsule, suppository, creams, lotions, solutions, gels, and pastes.

46. The composition of claim 45, wherein the solution comprises a sterile injectable solution.

47. The composition of claim 45, wherein the dosage form is further selected from the group consisting of immediate release, sustained release, and delayed release.

48. The composition of claim 45, further comprising an agent selected from the group consisting of an excipient, a lubricant, a wetting agent, an emulsifier, a penetration enhancer, a suspending agent, a preservative, and a flavoring agent.

49. The composition of claim 48, wherein the excipient comprises lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, or methyl cellulose.

50. The composition of claim 49, wherein the lubricant comprises talc, magnesium stearate, or mineral oil.

51. The composition of claim 48, wherein the penetration enhancer comprises isostearic acid, octanoic acid, oleic acid, oleyl alcohol, lauryl alcohol, ethyl oleate, isopropyl myristate, butyl stearate, methyl laurate, diisopropyl adipate, glyceryl monolaurate, tetrahydrofurfuryl alcohol polyethylene glycol ether, polyethylene glycol, propylene glycol, 2-(2-ethoxyethoxy)ethanol, diethylene glycol monomethyl ether, alkylaryl ethers of polyethylene oxide, polyethylene oxide monomethyl ethers, polyethylene oxide dimethyl ethers, dimethyl sulfoxide, glycerol, ethyl acetate, acetoacetic ester, N-alkylpyrrolidone, or terpenes.

52. A method of preventing the conversion of dihydrotestosterone to testosterone in the skin of a mammal, comprising:

administering a testosterone composition to the skin; and administering a 5α-reductase inhibitor composition to the skin.

53. A method of arresting or reducing cancer cell growth in a mammal comprising:

administering a testosterone composition to said mammal; and administering a 5α-reductase inhibitor composition to said mammal.

54. A method of reducing weight in a mammal comprising:

administering a testosterone composition to said mammal; and administering a 5α-reductase inhibitor composition to said mammal.

55. A method of inhibiting lipid production in a cell comprising:

administering a testosterone composition to said cell; and administering a 5α-reductase inhibitor composition to said cell.

56. A method of reducing hair loss in a human comprising:

administering a testosterone composition to said human; and administering a 5α-reductase inhibitor composition to said human.

57. A method of treating skin disorders in a human comprising:

administering a testosterone composition to said human; and administering a 5α-reductase inhibitor composition to said human.

* * * * *